US012558016B2

(12) United States Patent
Zhang et al.

(10) Patent No.: US 12,558,016 B2
(45) Date of Patent: Feb. 24, 2026

(54) PREMATURE BEAT DETECTION METHOD, ELECTRONIC DEVICE AND MEDIUM

(71) Applicant: HUAWEI TECHNOLOGIES CO., LTD., Shenzhen (CN)

(72) Inventors: Jie Zhang, Shenzhen (CN); Xi Huang, Shenzhen (CN); Hongbao Li, Shenzhen (CN); Jingwen Fan, Shanghai (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 474 days.

(21) Appl. No.: 17/926,518

(22) PCT Filed: May 19, 2021

(86) PCT No.: PCT/CN2021/094485
§ 371 (c)(1),
(2) Date: Nov. 18, 2022

(87) PCT Pub. No.: WO2021/233319
PCT Pub. Date: Nov. 25, 2021

(65) Prior Publication Data
US 2023/0190170 A1     Jun. 22, 2023

(30) Foreign Application Priority Data

May 20, 2020     (CN) ......................... 202010432393.9

(51) Int. Cl.
*A61B 5/364*          (2021.01)
*A61B 5/00*           (2006.01)
                      (Continued)

(52) U.S. Cl.
CPC .......... *A61B 5/364* (2021.01); *A61B 5/02416* (2013.01); *A61B 5/28* (2021.01);
(Continued)

(58) Field of Classification Search
CPC ....... A61B 5/02416; A61B 5/28; A61B 5/349; A61B 5/353; A61B 5/0006; A61B 5/0205; A61B 5/1455; A61B 5/6803; A61B 5/681
See application file for complete search history.

(56) References Cited

U.S. PATENT DOCUMENTS

2012/0101541 A1     4/2012   Corbucci et al.
2013/0023776 A1     1/2013   Olde et al.
(Continued)

FOREIGN PATENT DOCUMENTS

CN     109953756 A     7/2019
JP     2006180979 A    7/2006

OTHER PUBLICATIONS

Han, Dong, et al. "Premature Atrial and Ventricular Contraction Detection Using Photoplethysmographic Data from a Smartwatch." Sensors, vol. 20, No. 19, Oct. 5, 2020, pp. 5683-5683, https://doi.org/10.3390/s20195683. (Year: 2020).*
(Continued)

*Primary Examiner* — Paula J Stice
(74) *Attorney, Agent, or Firm* — Leydig, Voit & Mayer, Ltd.

(57)                ABSTRACT

This application discloses a premature beat detection method, an electronic device. The premature beat detection method in this application includes: performing premature beat detection on a user by using a premature beat detection function; determining a premature beat type of the user by using a premature beat type determining function when detecting that the user has a premature beat by using the premature beat detection function, and calculating premature beat load of the user based on detection data obtained by the premature beat detection function; and reminding the user of a premature beat risk when the calculated premature beat load is greater than a premature beat load threshold
(Continued)

corresponding to the premature beat type determined by the premature beat type determining function.

20 Claims, 17 Drawing Sheets

(51) Int. Cl.

| | |
|---|---|
| *A61B 5/024* | (2006.01) |
| *A61B 5/28* | (2021.01) |
| *A61B 5/329* | (2021.01) |
| *A61B 5/33* | (2021.01) |
| *A61B 5/349* | (2021.01) |
| *A61B 5/353* | (2021.01) |

(52) U.S. Cl.
CPC ............... *A61B 5/329* (2021.01); *A61B 5/33* (2021.01); *A61B 5/349* (2021.01); *A61B 5/353* (2021.01); *A61B 5/742* (2013.01)

(56) References Cited

U.S. PATENT DOCUMENTS

| | | | |
|---|---|---|---|
| 2013/0116587 A1 | 5/2013 | Sornmo et al. |
| 2020/0100693 A1 | 4/2020 | Velo |

OTHER PUBLICATIONS

Bonomi, Alberto G., et al. "Atrial Fibrillation Detection Using a Novel Cardiac Ambulatory Monitor Based on Photo-Plethysmography at the Wrist." Journal of the American Heart Association, vol. 7, No. 15, Aug. 7, 2018, https://doi.org/10.1161/jaha.118.009351. (Year: 2018).*

Pereira, Tania, et al. "Photoplethysmography Based Atrial Fibrillation Detection: A Review." Npj Digital Medicine, vol. 3, No. 1, Jan. 10, 2020, https://doi.org/10.1038/s41746-019-0207-9. (Year: 2020).*

Solosenko, Andrius, et al. "Photoplethysmography-Based Method for Automatic Detection of Premature Ventricular Contractions." IEEE Transactions on Biomedical Circuits and Systems, vol. 9, No. 5, Oct. 2015, pp. 662-669, https://doi.org/10.1109/tbcas.2015.2477437. (Year: 2015).*

Dhar, Sandipan, et al. "Effortless Detection of Premature Ventricular Contraction Using Computerized Analysis of Photoplethysmography Signal." Sādhanā, vol. 47, No. 1, Jan. 27, 2022, https://doi.org/10.1007/s12046-021-01781-3. (Year: 2022).*

Avram, Robert, et al. "Validation of an Algorithm for Continuous Monitoring of Atrial Fibrillation Using a Consumer Smartwatch." Heart Rhythm, vol. 18, No. 9, Sep. 1, 2021, pp. 1482-1490. (Year: 2021).*

* cited by examiner

Premature atrial contraction,
P wave and a QRS complex
appear in advance

ECG diagram

Heart rate diagram

PPG diagram

Premature atrial
contraction, broad and
distorted waveform

Premature ventricular
contraction, broad and
distorted R wave

ECG diagram

Heart rate diagram

PPG diagram

Premature ventricular
contraction, periodic broad
wave with distortion

TO

TO

Atrial fibrillation,
narrow and
distorted

Premature ventricular
contraction, broad
and distorted

Atrial fibrillation,
narrow and
distorted

PREMATURE BEAT DETECTION METHOD, ELECTRONIC DEVICE AND MEDIUM

This application is a National Stage of International Application No. PCT/CN2021/094485, filed on May 19, 2021, which claims priority to Chinese Patent Application No. 202010432393.9, filed on May 20, 2020, both of which are hereby incorporated by reference in their entireties.

TECHNICAL FIELD

This application relates to the field of information processing technologies, and in particular, to a premature beat detection method, an electronic device, and a medium.

BACKGROUND

A prevalence rate of cardiovascular diseases in China is continuously on the rise. At present, the quantity of patients in China is 290 million, and about 3.5 million people die of cardiovascular diseases every year. A mortality rate of cardiovascular diseases ranks first, and is higher than that of tumors and other diseases. In every 100,000 rural and urban residents, there are respectively 143.72 deaths and 136.21 deaths due to heart diseases, which pose a serious threat on the health of people in China. The heart disease has characteristics of high suddenness, a high fatality rate, and easy relapse, and has become a top killer of human health.

Arrhythmia is one of most common heart diseases. Arrhythmia means any abnormality in a frequency, a rhythm, an origin, a conduction speed, an excitation sequence, an atrioventricular conduction pathway, and the like of cardiac impulses. Arrhythmia is usually detected by using an electrocardiograph. An electrocardiograph (ECG) is reflection of an electrical activity of a heart on a human body surface. It is an important basis for detection and diagnosis of arrhythmia, and is also a main technical means for diagnosis of other heart diseases. With the development of technologies, more research teams and medical device companies have begun to use a photoplethysmography (PPG) detection technology for arrhythmia screening. Research in this aspect first focuses on atrial fibrillation (AF) detection, and gradually spreads to premature beats and other arrhythmia. Currently, an increasing quantity of watches are provided with ECG and PPG detection capabilities. ECG measurement can be implemented a single time by putting both hands together. However, using a watch for detection to perform continuous ECG measurement has excessively poor user experience; and a PPG detection technology can be used to perform continuous measurement without feeling by a user, to implement early screening of atrial fibrillation and premature beats, but PPG has its limitation in detecting arrhythmia, particularly with inability to differentiate between premature atrial contraction (PAC) and premature ventricular contraction (PVC).

SUMMARY

Embodiments of this application provide a premature beat detection method, an electronic device, and a medium, to avoid a disadvantage that a single detection function of an electronic device can continuously perform premature beat detection but cannot identify a premature beat type, and to comprehensively use two detection functions to achieve continuous premature beat detection and premature beat type determining, thereby achieving differentiated risk reminders for two types of premature beats, and avoiding a large quantity of false reminders or insufficient knowledge of a risk.

According to a first aspect, an embodiment of this application discloses a premature beat detection method, including: an electronic device performs premature beat detection on a user by using a premature beat detection function, to obtain first detection data; the electronic device determines a premature beat type of the user by using a premature beat type determining function when determining, based on the first detection data, that the user has a premature beat, and calculates premature beat load of the user based on second detection data obtained by the premature beat detection function; and the electronic device reminds the user of a premature beat risk when the calculated premature beat load is greater than a premature beat load threshold corresponding to the premature beat type determined by the premature beat type determining function. The first detection data is data for detecting a premature beat symptom, and the second detection data is data for calculating the premature beat load. Both of them are detection data obtained by using a premature beat detection function, and may be the same or different.

For example, a PPG sensor is used to continuously perform detection on the user to detect whether the user has a premature beat. When the user has a premature beat, an ECG is enabled to determine the premature beat type of the user. If it is determined that the premature beat type is premature atrial contraction, the user is reminded of a premature beat risk when the premature beat load is greater than a premature atrial contraction threshold. If it is determined that the premature beat type is premature ventricular contraction, the user is reminded of a premature beat risk when the premature beat load is greater than a premature ventricular contraction threshold. If it is determined that both premature atrial contraction and premature ventricular contraction exist, premature beat load combination is performed for comparison with a combined threshold, to determine whether to remind the user of a premature beat risk. The premature beat detection function (for example, by using the PPG sensor) is used to continuously perform detection on the user, the premature beat type is determined by using the premature beat type determining function (for example, ECG detection) after a premature beat is detected, and then it is determined whether the premature beat load exceeds the premature ventricular contraction threshold or the premature atrial contraction threshold, to achieve differentiated risk reminders for two types of premature beats, and avoid a large quantity of false reminders or insufficient knowledge of a risk.

In an implementation of the first aspect, the calculating premature beat load of the user based on second detection data obtained by the premature beat detection function includes: the electronic device determines, based on the premature beat type determined by using the premature beat type determining function, a shape of a unit wave that corresponds to the determined premature beat type and that is in a waveform of the first detection data; the electronic device matches, based on the determined shape of the unit wave, a unit wave that corresponds to the determined premature beat type and that is in a waveform corresponding to the second detection data; and the electronic device calculates the premature beat load of the user based on the matched unit wave corresponding to the determined premature beat type.

For example, after the premature beat type is determined by using an ECG, a unit wave in a waveform of PPG data generated at the same time as a unit wave that corresponds to the premature atrial contraction/premature ventricular contraction and that is in a waveform of ECG detection data is a premature atrial contraction/premature ventricular contraction unit wave. Then, all unit waves of this shape in the waveform of the PPG data detected in a specific time period are matched, to calculate the premature beat load. When a premature beat occurs, shapes of unit waves generated in PPG waveforms by premature beats of a same type are different for different persons due to different occurrence positions of premature beats, different transmission paths, different cardiac systole statuses, and different pulse wave transmission channels of the user. It is relatively difficult to identify premature beat types of different populations only by using the PPG waveform. An ECG is used to assist in determining whether a premature beat type existing in the detected PPG data is premature atrial contraction or premature ventricular contraction, so as to determine a shape of a waveform of a premature atrial contraction or premature ventricular contraction unit wave in a waveform of the PPG data obtained for the currently detected user, and further calculate the premature beat load, thereby improving calculation accuracy of the premature beat load.

In an implementation of the first aspect, the premature beat load is a percentage of a quantity of matched unit waves corresponding to the determined premature beat type in a total quantity of unit waves in the waveform of the detection data. For example, if there are 10,000 unit waves in the waveform of the detection data and 400 premature ventricular contraction unit waves, premature ventricular contraction load is 4%.

In an implementation of the first aspect, that the electronic device determines a premature beat type of the user by using a premature beat type determining function when determining, based on the first detection data, that the user has a premature beat includes: when determining, based on the first detection data, that the user has a premature beat, the electronic device determines whether the premature beat load is less than the premature atrial contraction threshold; and when the premature beat load is less than the premature atrial contraction threshold, the electronic device enables the premature beat type determining function to determine the premature beat type of the user. The premature beat type includes premature atrial contraction and premature ventricular contraction, and the premature atrial contraction threshold is greater than the premature ventricular contraction threshold.

In an implementation of the first aspect, the method further includes: when the premature beat load is greater than the premature atrial contraction threshold, the electronic device reminds the user of a premature beat risk. The premature atrial contraction threshold is much greater than the premature ventricular contraction threshold, for example, the premature atrial contraction threshold is 10%, and the premature ventricular contraction threshold is 0.5%. Therefore, if it is detected that the premature beat load is greater than the premature atrial contraction threshold by using the premature beat detection function, regardless of whether the premature beat is premature atrial contraction or premature ventricular contraction, it can be determined that a premature beat symptom of the user is severe, and the user needs to be reminded of a premature beat risk.

In an implementation of the first aspect, that the electronic device determines a premature beat type of the user by using a premature beat type determining function when determining, based on the first detection data, that the user has a premature beat includes: when determining, based on the first detection data, that the user has a premature beat, the electronic device calculates whether the premature beat load is greater than an enabling threshold; and when the premature beat load is greater than the enabling threshold, enables the premature beat type determining function to determine the premature beat type of the user. The premature beat type includes premature atrial contraction and premature ventricular contraction, the premature atrial contraction threshold is greater than the premature ventricular contraction threshold, and the premature ventricular contraction threshold is greater than the enabling threshold.

In other words, when it is detected by using the premature beat detection function that the user has a premature beat, the premature beat type is not determined first, and instead, the premature beat detection function is enabled only when the premature beat load is greater than the enabling threshold, where the enabling threshold is less than a premature ventricular contraction threshold. In this solution, the premature beat type determining function may be automatically enabled when the electronic device determines that the premature beat load is greater than the enabling threshold, or may be enabled by reminding the user when it is determined that the premature beat load is greater than the enabling threshold.

In an implementation of the first aspect, that the electronic device determines a premature beat type of the user by using a premature beat type determining function when determining, based on the first detection data, that the user has a premature beat includes: when detecting, by using the premature beat detection function, that the user has a premature beat, the electronic device reminds the user to enable the premature beat type determining function; and when receiving an enabling instruction of enabling the premature beat type determining function from the user, the electronic device enables the premature beat type determining function.

In an implementation of the first aspect, the electronic device determines, in the following manner, whether the calculated premature beat load is greater than the premature beat load threshold corresponding to the premature beat type determined by using the premature beat type determining function: when the premature beat type determined by using the premature beat type determining function includes only premature atrial contraction, determining whether the calculated premature beat load is greater than the premature atrial contraction threshold; when the premature beat type determined by using the premature beat type determining function includes only premature ventricular contraction, determining whether the calculated premature beat load is greater than the premature ventricular contraction threshold; or when the premature beat type determined by using the premature beat type determining function includes premature atrial contraction and premature ventricular contraction, determining whether combined load of calculated premature atrial contraction load and premature ventricular contraction load is greater than the combined threshold. The combined load is greater than the premature atrial contraction load, or the combined load is greater than the premature ventricular contraction load. In addition, the premature atrial contraction threshold is greater than the combined threshold, and the combined threshold is greater than the premature ventricular contraction threshold.

In this solution, the combined load may be obtained by converting the premature ventricular contraction load into the premature atrial contraction load, or may be obtained by converting the premature atrial contraction load into the premature ventricular contraction load, and the combined threshold may be obtained by converting the premature ventricular contraction threshold into the premature atrial contraction threshold or converting the premature atrial contraction threshold into the premature ventricular contraction threshold.

In an implementation of the first aspect, the electronic device includes a photoplethysmography sensor and an electrocardiography sensor, the photoplethysmography sensor implements the premature beat detection function, and the electrocardiography sensor implements the premature beat type determining function.

In an implementation of the first aspect, the method further includes: when the electronic device determines to remind the user of a premature beat risk, the electronic device displays premature beat risk reminder information. In another embodiment, the electronic device may alternatively remind the user of a premature beat risk in a manner such as voice, which is not limited to a form of displaying the premature beat risk reminder information on a display of the electronic device.

According to a second aspect, an embodiment of this application discloses a premature beat detection method, including: a second electronic device obtains, from a first electronic device, first detection data obtained by the first electronic device by performing premature beat detection on a user by using a premature beat detection function; the second electronic device sends an enabling instruction when determining, based on the received first detection data, that the user has a premature beat, where the enabling instruction is used to instruct the first electronic device to enable a premature beat type determining function; the second electronic device receives, from the first electronic device, second detection data obtained by the first electronic device by using the premature beat detection function and determining data obtained by using the premature beat type determining function; the second electronic device determines a premature beat type of the user based on the determining data, and calculates premature beat load of the user based on the second detection data; and when the calculated premature beat load is greater than a premature beat load threshold corresponding to the determined premature beat type, the second electronic device determines to remind the user of a premature beat risk.

In this solution, the premature beat detection function (for example, by using a PPG sensor) is also used to continuously perform detection on the user, and after a premature beat is detected, the premature beat type determining function (for example, ECG detection) is used to determine whether the premature beat load exceeds a premature ventricular contraction threshold or a premature atrial contraction threshold, to achieve differentiated risk reminders for two types of premature beats, and avoid a large quantity of false reminders or insufficient knowledge of a risk. A difference from the first aspect is that the first electronic device (for example, a wearable electronic device) performs only premature beat detection and premature beat type determining, and the second electronic device (for example, a mobile phone or a server) implements determining of whether there is a premature beat, calculation of premature beat load, and comparison between the premature beat load and the premature beat threshold. This alleviates calculation load of the first electronic device, and reduces a requirement for a calculation capability of the first electronic device. In addition, when determining that the user has a premature beat, the second electronic device may directly send the enabling instruction to the first electronic device, or may send the enabling instruction or enabling prompt information

6 tion to the user so that the user enables the premature beat type determining function of the first electronic device.

In an implementation of the second aspect, the calculating premature beat load of the user based on the second detection data includes: the second electronic device determines, based on the determined premature beat type, a shape of a unit wave that corresponds to the determined premature beat type and that is in a waveform of the first detection data; the second electronic device matches, based on the determined shape of the unit wave, a unit wave that corresponds to the determined premature beat type and that is in a waveform corresponding to the second detection data; and the second electronic device calculates the premature beat load of the user based on the matched unit wave corresponding to the determined premature beat type. The premature beat load is a percentage of a quantity of matched unit waves corresponding to the determined premature beat type in a total quantity of unit waves in the waveform of the second detection data.

For example, the mobile phone determines the premature beat type based on ECG data detected by a wearable device by using an ECG, and then the mobile phone determines that a unit wave in a waveform of PPG data generated at the same time as a unit wave that corresponds to premature atrial contraction/premature ventricular contraction and that is in a waveform of ECG detection data is a premature atrial contraction/premature ventricular contraction unit wave. Then, all unit waves of this shape in the waveform of the PPG data detected in a specific time period are matched, to calculate the premature beat load.

When a premature beat occurs, shapes of unit waves generated in PPG waveforms by premature beats of a same type are different for different persons due to different occurrence positions of premature beats, different transmission paths, different cardiac systole statuses, and different pulse wave transmission channels of the user. It is relatively difficult to identify premature beat types of different populations only by using the PPG waveform. An ECG is used to assist in determining whether a premature beat type existing in the detected PPG data is premature atrial contraction or premature ventricular contraction, so as to determine a shape of a waveform of a premature atrial contraction or premature ventricular contraction unit wave in a waveform of the PPG data obtained for the currently detected user, and further calculate the premature beat load, thereby improving calculation accuracy of the premature beat load.

In an implementation of the second aspect, that the second electronic device sends an enabling instruction when determining, based on the received first detection data, that the user has a premature beat includes: when determining, based on the first detection data, that the user has a premature beat, the second electronic device determines whether the premature beat load is less than a premature atrial contraction threshold; and when the premature beat load is less than the premature atrial contraction threshold, the second electronic device sends the enabling instruction. The premature beat type includes premature atrial contraction and premature ventricular contraction, and the premature atrial contraction threshold is greater than a premature ventricular contraction threshold.

In an implementation of the second aspect, the method further includes: when the premature beat load is greater than the premature atrial contraction threshold, the second electronic device reminds the user of a premature beat risk. The premature atrial contraction threshold is much greater than the premature ventricular contraction threshold, for example, the premature atrial contraction threshold is 10%, and the premature ventricular contraction threshold is 0.5%. Therefore, if it is detected that the premature beat load is greater than the premature atrial contraction threshold by using the premature beat detection function, regardless of whether the premature beat is premature atrial contraction or premature ventricular contraction, it can be determined that a premature beat symptom of the user exists, and the user needs to be reminded of a premature beat risk.

In an implementation of the second aspect, that the second electronic device sends an enabling instruction when determining, based on the received first detection data, that the user has a premature beat includes: when determining, based on the first detection data, that the user has a premature beat, the second electronic device calculates whether the premature beat load is greater than an enabling threshold; and when the premature beat load is greater than the enabling threshold, sends the enabling instruction. The premature beat type includes premature atrial contraction and premature ventricular contraction, the premature atrial contraction threshold is greater than the premature ventricular contraction threshold, and the premature ventricular contraction threshold is greater than the enabling threshold.

In an implementation of the second aspect, the second electronic device determines, in the following manner, whether the calculated premature beat load is greater than the premature beat load threshold corresponding to the determined premature beat type: when the determined premature beat type includes only premature atrial contraction, the second electronic device determines whether the calculated premature beat load is greater than the premature atrial contraction threshold; when the determined premature beat type includes only premature ventricular contraction, the second electronic device determines whether the calculated premature beat load is greater than the premature ventricular contraction threshold; or when the determined premature beat type includes premature atrial contraction and premature ventricular contraction, the second electronic device determines whether combined load of calculated premature atrial contraction load and premature ventricular contraction load is greater than a combined threshold. The combined load is greater than the premature atrial contraction load, or the combined load is greater than the premature ventricular contraction load. In addition, the premature atrial contraction threshold is greater than the combined threshold, and the combined threshold is greater than the premature ventricular contraction threshold.

In this solution, the combined load may be obtained by converting the premature ventricular contraction load into the premature atrial contraction load, or may be obtained by converting the premature atrial contraction load into the premature ventricular contraction load, and the combined threshold may be obtained by converting the premature ventricular contraction threshold into the premature atrial contraction threshold or converting the premature atrial contraction threshold into the premature ventricular contraction threshold.

In an implementation of the second aspect, the method further includes: when the second electronic device determines to remind the user of a premature beat risk, the second electronic device displays premature beat risk reminder information.

According to a third aspect, an embodiment of this application discloses a premature beat detection method, including: a first electronic device performs premature beat detection on a user by using a premature beat detection function; the first electronic device sends first detection data obtained by using the premature beat detection function to a second electronic device; the first electronic device receives an enabling instruction from the second electronic device; the first electronic device enables a premature beat type determining function in response to the enabling instruction; and the first electronic device sends, to the second electronic device, second detection data obtained by using the premature beat detection function and determining data obtained by using the premature beat type determining function.

In an implementation of the third aspect, the method further includes: the first electronic device receives premature beat risk reminder information from the second electronic device; and the first electronic device displays the risk reminder information.

In an implementation of the third aspect, the first electronic device includes a photoplethysmography sensor and an electrocardiography sensor, the photoplethysmography sensor implements the premature beat detection function, and the electrocardiography sensor implements the premature beat type determining function.

According to a fourth aspect, an embodiment of this application discloses a premature beat detection method, including: a first electronic device performs premature beat detection on a user by using a premature beat detection function; when detecting, by using the premature beat detection function, that the user has a premature beat, the first electronic device sends an enabling instruction to a second electronic device, where the enabling instruction is used to instruct the second electronic device to determine a premature beat type of the user by using a premature beat type determining function; and the first electronic device reminds the user of a premature beat risk when premature beat load calculated based on detection data obtained by using the premature beat detection function is greater than a premature beat load threshold corresponding to the premature beat type determined by the second electronic device by using the premature beat type determining function.

The premature beat detection function (for example, by using a PPG sensor) of one electronic device is used to continuously perform detection on the user, the premature beat type is determined by using the premature beat type determining function (for example, ECG detection) of another device after a premature beat is detected, and then it is determined whether the premature beat load exceeds a premature ventricular contraction threshold or a premature atrial contraction threshold, to achieve differentiated risk reminders for two types of premature beats, and avoid a large quantity of false reminders or insufficient knowledge of a risk. For example, the first electronic device is an electronic mattress, and the electronic mattress has a seismocardiogram (Seismocardiogram, SCG) detection function, namely, a premature beat detection function. The second electronic device is a watch 100, which has an ECG function, namely, a premature beat type determining function.

According to a fifth aspect, an embodiment of this application discloses a computer-readable medium. The computer-readable medium stores instructions, and when the instructions are run on a machine, the machine is enabled to perform the premature beat detection method according to any one of the foregoing first to fourth aspects.

According to a sixth aspect, an embodiment of this application discloses an electronic device. The electronic device includes: a memory, configured to store instructions executed by one or more processors in a system, and the processor, as one of processors of the electronic device, configured to perform the premature beat detection method according to any one of the foregoing first to fourth aspects.

In an implementation of the sixth aspect, the electronic device further includes a photoplethysmography sensor and an electrocardiography sensor, the photoplethysmography sensor implements the premature beat detection function, and the electrocardiography sensor implements the premature beat type determining function.

According to a seventh aspect, an embodiment of this application discloses an electronic device. The electronic device has functions of electronic devices for implementing the foregoing premature beat detection method. The functions may be implemented by hardware, or may be implemented by hardware executing corresponding software. The hardware or the software includes one or more modules corresponding to the functions.

BRIEF DESCRIPTION OF DRAWINGS

FIG. 4a-1 and FIG. 4a-2 are a schematic flowchart of a premature beat detection method according to an embodiment of this application;

FIG. 4b-1 and FIG. 4b-2 are a schematic flowchart of a premature beat detection method according to an embodiment of this application;

FIG. 4c-1 and FIG. 4c-2 are a schematic flowchart of a premature beat detection method according to an embodiment of this application;

DESCRIPTION OF EMBODIMENTS

The technical solutions in embodiments of this application are further described below in detail with reference to accompanying drawings and embodiments.

Figure 1:
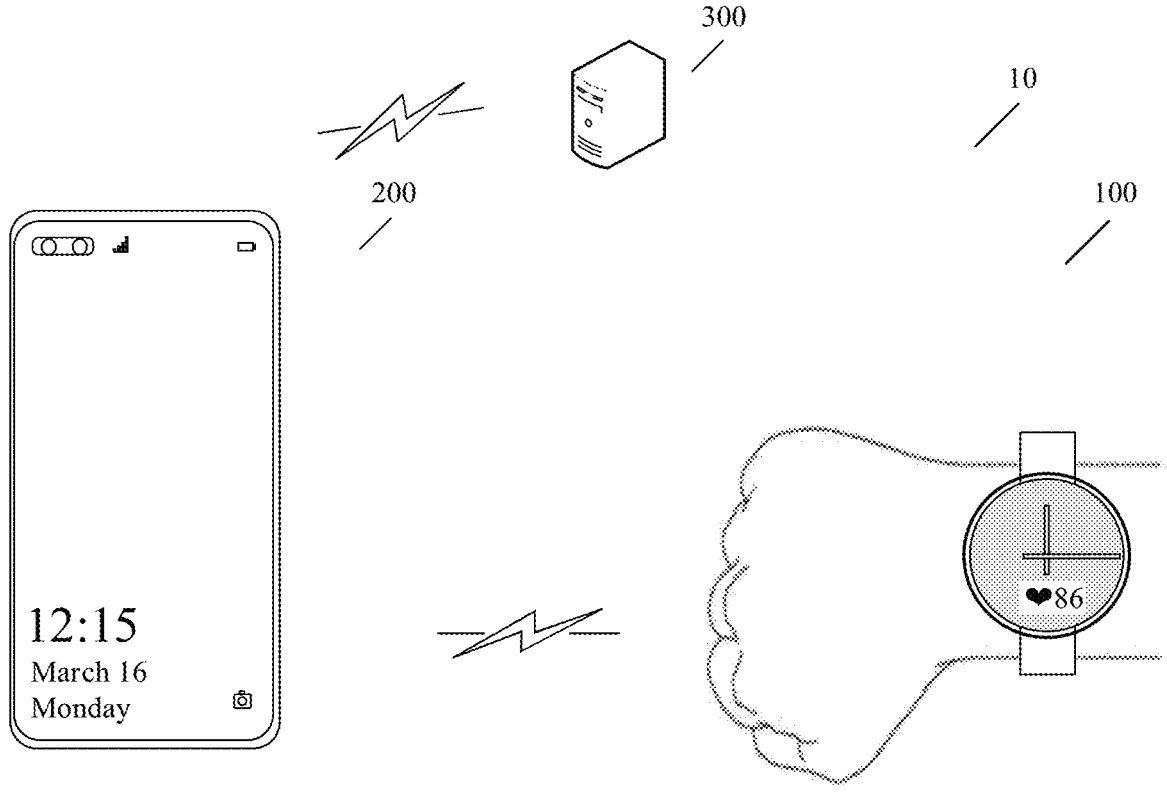
FIG. 1 is a scenario diagram of a premature beat detection method according to an embodiment of this application.

FIG. 1 is a scenario diagram of a premature beat detection method according to an embodiment of this application. As shown in FIG. 1, this embodiment of this application relates to an intelligent wearable device 100. The intelligent wearable device 100 may perform wireless communication with another electronic device in various wireless manners, for example, perform wireless communication with an electronic device 200 or a server 300. For example, the intelligent wearable device 100 may send a wireless signal to the server 300 through a wireless communications link by using its radio frequency circuit and antenna, to request the server 300 to process a specific service requirement of the intelligent wearable device 100, such as user registration, and data obtaining and detection. For another example, the intelligent wearable device 100 may perform pairing with the electronic device 200 by using its Bluetooth, and after the pairing succeeds, perform data communication with the electronic device 200 through a Bluetooth communications link. Certainly, the electronic device 100 may perform data communication with the electronic device 200 in another wireless communication manner, such as a radio-frequency identification technology, a short-range wireless communication technology, or wireless fidelity (Wi-Fi).

The intelligent wearable device 100 has a biological detection device (such as an ECG sensor) that is capable of only determining a premature beat type but has difficulty in performing continuous premature beat load detection, and a biological detection device (such as a PPG sensor) that is capable of performing continuous premature beat load detection but cannot determine the premature beat type. In this application, advantages of two different types of premature beat detection are combined, to obtain a premature beat detection result rivaling a continuous photoplethysmography detection function. To be specific, the user is reminded of differentiated risks based on premature beat types (such as premature atrial contraction and premature ventricular contraction) and premature beat load. For example, in specific implementation, the intelligent wearable device 100 may obtain physiological data of the user, such as photoplethysmograph (PPG) data or electrocardiograph (ECG) data, determine whether the user has a premature beat based on the obtained PPG data, determine a premature beat type based on the ECG data, then calculate premature beat load such as premature atrial contraction load or premature ventricular contraction by using the intelligent wearable device 100 or the electronic device 200 based on continuously measured PPG data, and finally remind the user of risks based on different types of premature beat load. For example, if the premature beat type is premature atrial contraction and the premature atrial contraction load is greater than a premature atrial contraction threshold, the intelligent wearable device 100 reminds the user of a high risk. If the premature beat type is premature ventricular contraction and the premature ventricular contraction load is greater than a premature ventricular contraction threshold, the intelligent wearable device 100 reminds the user of a high risk. If the premature beat type includes both premature atrial contraction and premature ventricular contraction and combined premature beat load of the premature atrial contraction load and the premature ventricular contraction load is greater than a combined premature beat threshold, the intelligent wearable device 100 reminds the user of a high risk. In this technical solution of this application, advantages of PPG detection and ECG detection can be comprehensively used, to avoid that the premature beat type cannot be determined by using PPG detection and ECG detection is not convenient for continuous premature beat load detection, achieve differentiated risk reminders for two types of premature beats, and avoid a large quantity of false reminders or insufficient knowledge of a risk.

In a specific embodiment of this application, the intelligent wearable device 100 may be various devices, including but not limited to, wearable electronic devices such as watches, wristbands, glasses, helmets, or headbands, medical testing instruments, and the like. In the following description, for ease of description, a watch 100 is used as an example in the technical solutions of this application.

The electronic device 200 may be a client capable of communicating with the intelligent wearable device 100, and can help the intelligent wearable device 100 implement registration, control firmware update of the intelligent wearable device 100, receive detection data of the intelligent wearable device 100, and assist the intelligent wearable device 100 in analyzing historical detection data. It can be understood that the electronic device 200 may include but is not limited to, a laptop computer, a desktop computer, a tablet computer, a smartphone, a server, a wearable device, a head mounted display, a mobile email device, a portable game console, a portable music player, a reader device, a television in which one or more processors are embedded or coupled, or another electronic device capable of accessing a network. In the following description, for ease of description, a mobile phone 200 is used as an example in the technical solutions of this application.

Figure 2:
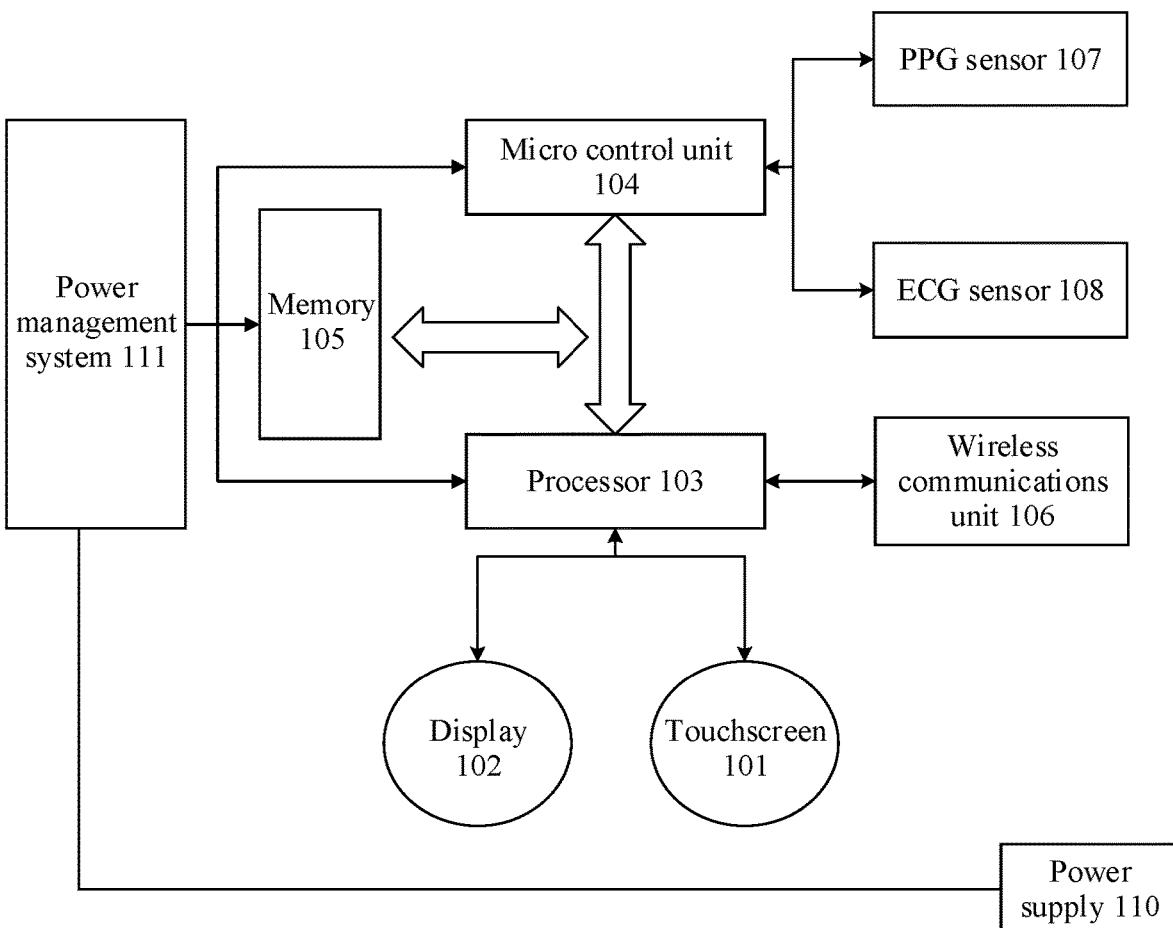
FIG. 2 is a schematic diagram of a hardware structure of a watch according to an embodiment of this application.

FIG. 2 is a schematic diagram of a hardware structure of a watch 100 according to some embodiments of this application. The watch may include a main body of the watch 100. In an embodiment of this application, the main body of the watch 100 may include a touchscreen 101 (also referred to as a touch panel), a display 102, a housing (the housing includes a front cover (not shown in FIG. 2) and a bottom cover (not shown in FIG. 2)), a processor 103, a micro control unit (MCU) 104, a memory 105, a wireless communications unit 106, a PPG sensor 107, an ECG sensor 108, a power supply 110, a power management system 111, and the like.

The following separately describes functional components of the watch 100.

The touchscreen 101, which may also be referred to as a touch panel, may collect a touch operation performed by a watch user on the touch panel (for example, an operation performed by the user on the touch panel or near the touch panel by using any appropriate object or accessory such as a finger or a stylus) and drive a corresponding connection apparatus based on a preset program.

The display 102 may be configured to display information entered by the user or prompt information provided for the user and various menus on the watch. Further, the touchscreen 101 can cover the display 102. When detecting a touch operation on or near the touchscreen 101, the touchscreen 101 transmits the touch operation to the processor 103 to determine a type of a touch event. Then, the processor 103 provides corresponding visual output on the display 102 based on the type of the touch event. For example, in some embodiments of this application, the watch 100 detects PPG data of the user and determines that the user has a premature beat, and can display, on the display 102, information reminding the user of a premature beat risk.

The processor 103 is configured to perform system scheduling, control the touchscreen 101 and the display 102, and support processing of the wireless communications unit 106, and so on.

The micro control unit 104 is configured to control a sensor, perform calculation on data of the sensor, and communicate with the processor 103, and so on. The sensor may include a PPG sensor 107, an ECG sensor 108, or another sensor. The PPG sensor can detect a pulse wave, a heart rate, a heartbeat interval, a respiration rate, blood pressure, cardiac efficiency, and a blood oxygen level of the user, and the like. The heartbeat interval and/or the pulse waveform in heart rhythm data may be used to determine a premature beat. For example, in some embodiments of this application, the micro control unit 104 analyzes data of the PPG sensor to determine whether a premature beat exists, and the micro control unit 104 analyzes data of the ECG sensor to determine a premature beat type such as premature ventricular contraction or premature atrial contraction. In addition, it can be understood that, in another embodiment, the foregoing processing of PPG data and ECG data may alternatively be implemented by the processor 103, which is not limited herein.

The memory 105 may be configured to store a software program and various data (such as various detection data of the watch 100). The processor 103 performs various functional applications of the watch 100 and processes data by running the software program and the data stored in the memory 105. For example, in some embodiments of this application, the memory 105 may store the PPG data collected by the PPG sensor or the ECG data collected by the ECG sensor. In addition, the memory may also store registration information, login information, and the like of the user.

The watch 100 implements wireless communication with another electronic device (such as a mobile phone or a tablet computer) through the wireless communications unit 106. For example, the wireless communication includes a wireless communication solution such as a wireless local area network (WLAN) (for example, a wireless fidelity (Wi-Fi) network), Bluetooth (BT), a global navigation satellite system (GNSS), frequency modulation (FM), a near field communication (NFC) technology, an infrared (IR) technology, or the like.

It can be understood that the structure shown in FIG. 2 is merely a specific structure for implementing a function of the watch 100 in the technical solutions of this application, and a watch 100 having another structure and capable of achieving a similar function is also applicable to the technical solutions of this application, which is not limited herein.

In the following embodiments, the technical solutions of this application are described by using an example in which the PPG sensor and the ECG sensor are used to detect a premature beat. It can be understood that, in another embodiment, the technical solutions of this application may be implemented alternatively by combining an ECG detection device and another device capable of performing continuous premature beat detection, which is not limited herein.

Figure 3A:
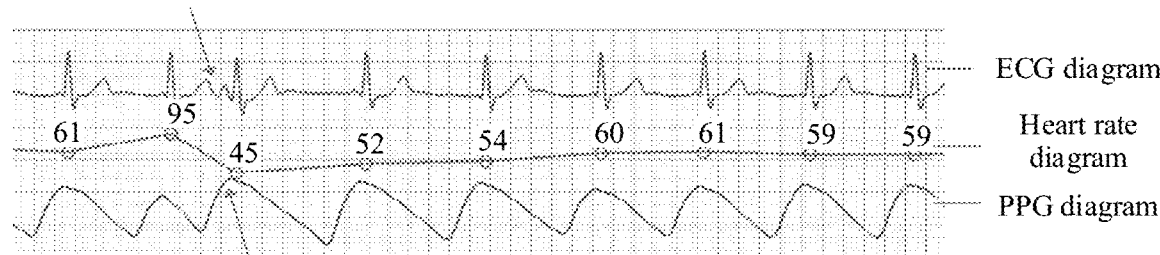
FIG. 3a is a schematic diagram of a premature atrial contraction waveform according to an embodiment of this application.
Figure 3B:
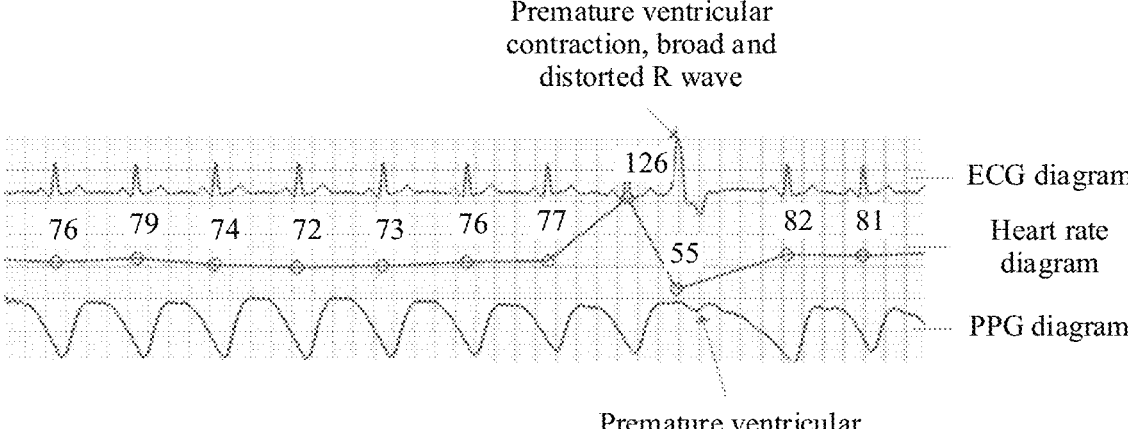
FIG. 3b is a schematic diagram of a premature ventricular contraction waveform according to an embodiment of this application.

Waveform diagrams of PPG data and ECG data related to a premature beat in embodiments of this application are described first. FIG. 3a and FIG. 3b show PPG waveform diagrams, ECG waveform diagrams, and heart rate diagrams in the case of premature atrial contraction and premature ventricular contraction, respectively.

As shown in FIG. 3a, when premature atrial contraction occurs during heart beating, a waveform in the ECG waveform diagram shows that a P wave and a QRS complex (QRS) appear in advance. The P wave is an atrial depolarization wave, and represents excitation of left and right atria. The QRS complex reflects change of depolarization potentials of the left and right ventricles with time. The first downward wave in the QRS complex is the Q wave, an upward wave is an R wave, and a next downward wave is an S wave. In the PPG waveform diagram, the waveform shows a broad distortion, and a main characteristic is that a previous waveform becomes smaller and an adjacent waveform becomes larger and a premature atrial contraction waveform randomly appears in the PPG waveform diagram. Alternatively, distorted waveforms and normal waveforms appear at intervals. For example, one normal wave and one distorted wave appear, and this phenomenon is referred to as "bigeminy". For another example, one distorted wave and two normal waves, or two distorted waves and one normal wave appear, and this phenomenon is referred to as "trigeminy".

As shown in FIG. 3b, when premature ventricular contraction occurs during heart beating, a unit wave in the ECG waveform diagram shows a broad distorted R wave, and a unit wave in the PPG waveform diagram shows a periodic broad wave with distortion. A main characteristic may be that two unit waves are combined and a premature ventricular contraction unit wave randomly appears in the PPG waveform diagram. Alternatively, distorted unit waves and normal unit waves appear at intervals. For example, one normal unit wave and one distorted unit wave appear, and this phenomenon is referred to as "bigeminy". For another example, one distorted unit wave and two normal unit waves, or two distorted unit waves and one normal unit wave appear, and this phenomenon is referred to as "trigeminy". It can be understood that, in this application, the unit wave refers to a waveform that can represent one heartbeat in waveforms of detection data obtained in various detection manners. For example, for a waveform of the PPG data, in a specific time period, a heart beats 100,000 times in total, which correspond to 100,000 PPG unit waves in a PPG waveform. In addition, it can be understood that, for a premature ventricular contraction waveform in a PPG waveform, two normal PPG unit waves may be combined so that it is difficult to decompose them into single unit waves. Therefore, when the detected premature beat type is premature ventricular contraction, a quantity of premature ventricular contraction waves matched in the PPG waveform multiplied by 2 may be used as a quantity of premature ventricular contraction unit waves. For example, it is found, by using ECG detection, that an existing premature beat is premature ventricular contraction, and in the PPG waveform, corresponding premature ventricular contraction waves each are obtained by combining two unit waves, where a quantity of the corresponding premature ventricular contraction waves is m. In this case, a quantity of unit waves corresponding to the premature ventricular contraction waves may be set to $2m$.

It should be noted that, for a same person, due to a fixed position of an abnormal pacemaker during premature beats, unit waves of premature beats (such as premature atrial contraction and premature ventricular contraction) can be determined in the PPG waveform diagram. However, people have individual differences, and most people have different positions of abnormal pacemakers during premature beats. Therefore, shapes of PPG unit waves produced by different people during premature beats are diversified. Whether a PPG unit wave of an existing premature beat is a premature atrial contraction unit wave or a premature ventricular contraction unit wave cannot be determined. Therefore, in this application, an ECG may be used to assist in determining whether a premature beat type existing in the detected PPG data is premature atrial contraction or premature ventricular contraction.

The following describes the technical solutions of this application in detail with reference to specific scenarios.

In some embodiments, the watch 100 monitors a heart rhythm status of the user, and determines whether the user has a premature beat based on PPG data detected by the watch 100. When a premature beat exists, ECG detection is enabled, to determine a premature beat type, and PPG detection is continuously performed. Then waveform matching is performed on the detected PPG data based on a shape (such as a shape of a premature atrial contraction unit wave or a shape of a premature ventricular contraction unit wave) of a PPG unit wave corresponding to the premature beat type determined by using an ECG, to match a unit wave that has the shape of the PPG unit wave of the determined premature beat type and that is in a PPG waveform of the PPG data. Then, load of different premature beat types is calculated based on a corresponding unit wave obtained through matching. Finally, the watch 100 reminds the user of premature beat risks based on different types of premature beat load. As shown FIG. 5a, when the watch 100 detects that the user is at risk of a premature beat (premature atrial contraction or premature ventricular contraction), an interface of the watch 100 displays "You have a premature beat symptom. Please seek medical attention in time" to remind the user of a premature beat risk. It can be understood that the watch 100 may remind the user of a premature beat risk in another form, such as providing vibration or a sound, which is not limited herein.

In addition, it can be understood that, in another embodiment, analysis of the PPG data and the ECG data may alternatively be performed by the mobile phone 200. For example, the watch 100 sends, through Bluetooth or in another wireless communication manner, the PPG data and the ECG data detected by the watch 100 to the mobile phone 200. Then the mobile phone 200 determines the premature beat type based on the received ECG data, and at the same time, marks PPG data of different premature beat types, to calculate different types of premature beat load. Finally, the mobile phone 100 reminds the user of premature beat risks based on different types of premature beat load. For ease of description, the following is described by using an example in which the watch 100 performs detection to obtain PPG data and ECG data, and processes and analyzes data, and finally the watch 100 performs premature beat risk reminding.

Figures 1, 2, 4A:
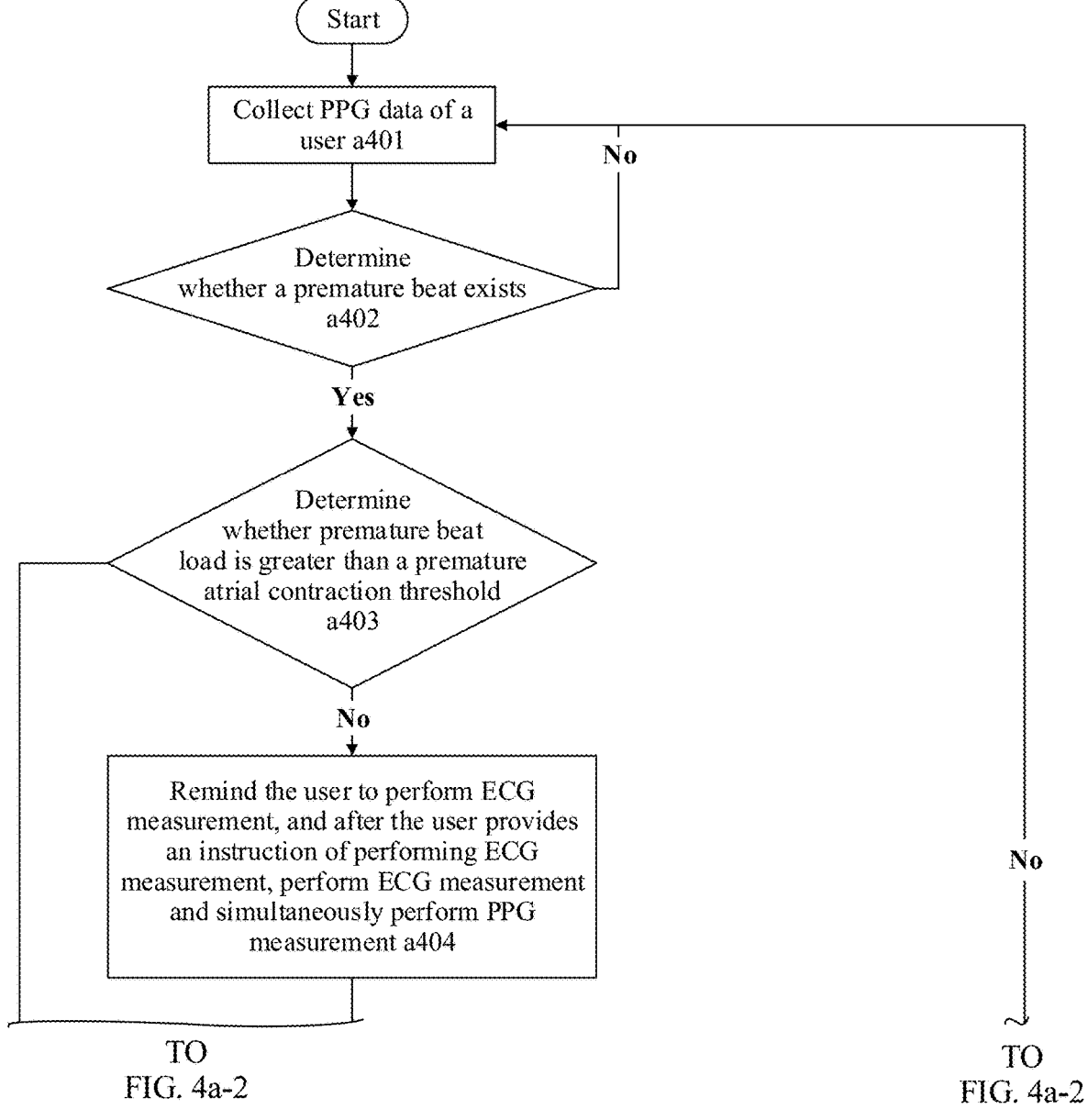
Figures 2, 4A:
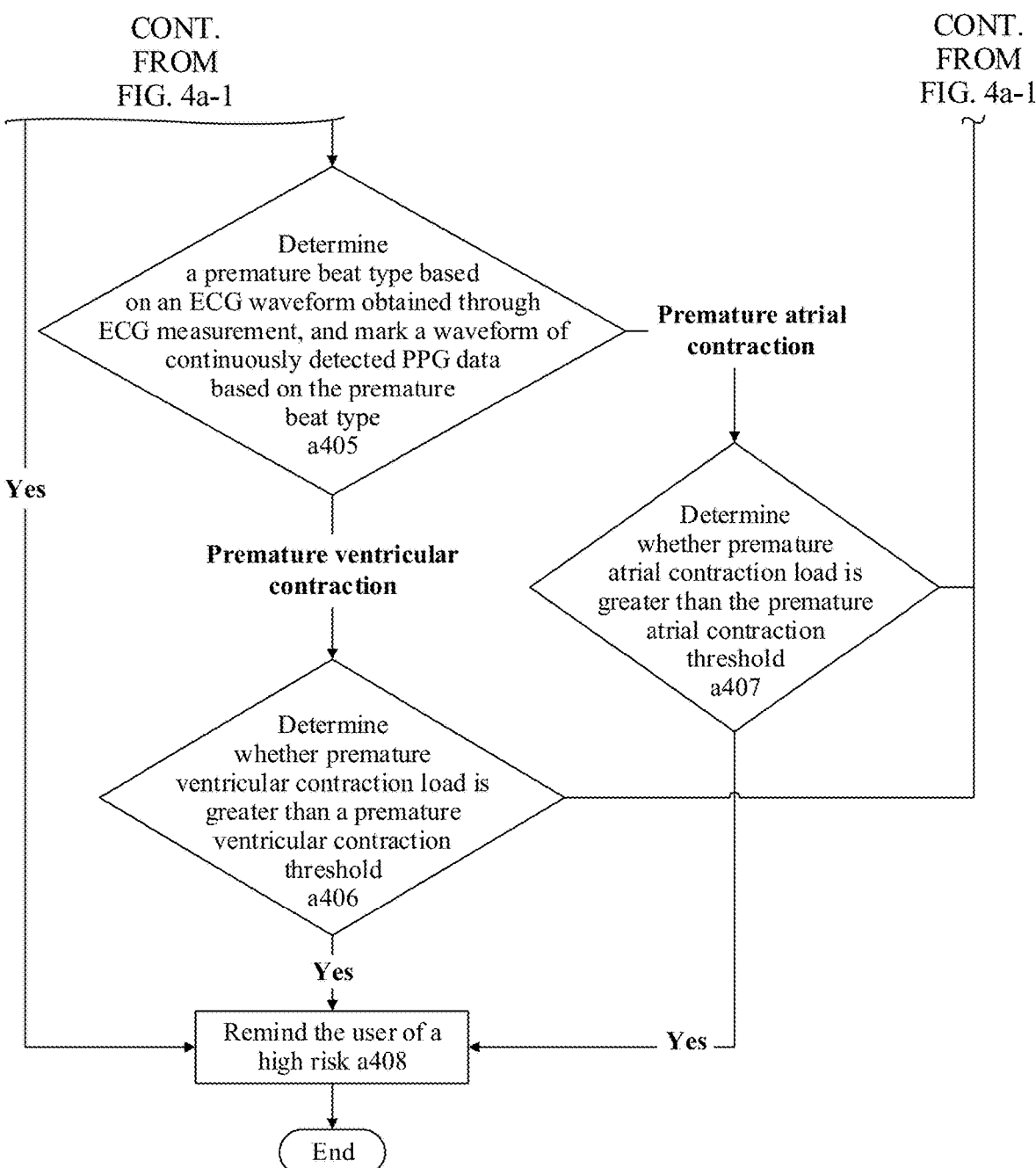

FIG. 4a-1 and FIG. 4a-2 are a schematic flowchart of a premature beat detection method according to some embodiments of this application. In the embodiment shown in FIG. 4a-1 and FIG. 4a-2, first, whether premature beat load detected by using PPG is greater than a premature atrial contraction threshold is directly determined. Treatment is generally needed when premature atrial contraction load is above 10% (namely, the premature atrial contraction threshold), and intervention is needed when premature ventricular contraction load is above 0.5% (premature ventricular contraction threshold). Therefore, when it is directly determined that the premature beat load is greater than the premature atrial contraction threshold, it can be determined that the premature beat load (whether it is premature atrial contraction load or premature ventricular contraction load) of the user is too high, and the user can be directly reminded of a premature beat risk. However, when the premature beat load is less than the premature atrial contraction threshold, an ECG is enabled to perform detection, so as to distinguish between premature beat types, and determine, by using different premature beat thresholds for different types, whether the user has a premature beat risk. It can be understood that values of the specific thresholds (such as a premature ventricular contraction threshold of 0.5% and a premature atrial contraction threshold of 10%) in this embodiment of this application are merely examples, and can be modified according to an actual requirement, which is not limited herein.

Specifically, as shown in FIG. 4a-1 and FIG. 4a-2, a procedure of the premature beat detection method includes the following steps.

a401: A watch 100 collects PPG data of a user.

a402: The watch 100 determines whether a premature beat exists. For example, the watch 100 performs continuous detection on the user, and determines the collected PPG data periodically or in real time to determine whether a premature beat exists. For example, the watch 100 determines whether a PPG waveform of the PPG data is abnormal based on the collected PPG data (refer to the descriptions of FIG. 3a and FIG. 3b).

If a premature beat exists, a403 is performed. Otherwise, a401 is continuously performed.

a403: The watch 100 determines whether premature beat load is greater than a premature atrial contraction threshold. The premature beat load may be obtained based on a percentage of a quantity of abnormal PPG unit waves in a PPG waveform of PPG data detected within a preset time in a quantity of all PPG unit waves in the PPG waveform. For example, in 24 hours, a heart beats 100,000 times in total, and there are 100,000 PPG unit waves in the PPG waveform. If there are 15,000 abnormal PPG unit waves, the premature beat load is 15%. It should be noted that premature atrial contraction may develop into atrial tachycardia and atrial fibrillation, premature ventricular contraction may develop into malignant and fatal arrhythmia such as ventricular tachycardia and ventricular fibrillation. Treatment is needed generally when premature atrial contraction is above 10%, and intervention is needed when premature ventricular contraction is above 0.5%. If a same risk threshold is set for both of them, and if the threshold is too low, the user may be reminded too frequently when a premature atrial contraction risk is relatively low. If the threshold is too high, a premature ventricular contraction risk may be underestimated, missing a best treatment window. In this embodiment of this application, the premature atrial contraction threshold is set to 10%, and the premature ventricular contraction threshold is set to 0.5%. These thresholds are obtained based on clinical data and are generally applicable. However, the premature atrial contraction threshold and the premature ventricular contraction threshold may be adjusted according to a specific requirement, which is not limited herein. It can be understood that there are 100,000 heartbeats and 15,000 abnormal PPG unit waves, which are merely examples, and other values may be used, which is not limited herein.

In addition, it can be understood that in another embodiment of this application, another manner in the conventional technology may also be used to calculate the premature beat load, which is not limited to the foregoing manner.

Figure 5A:
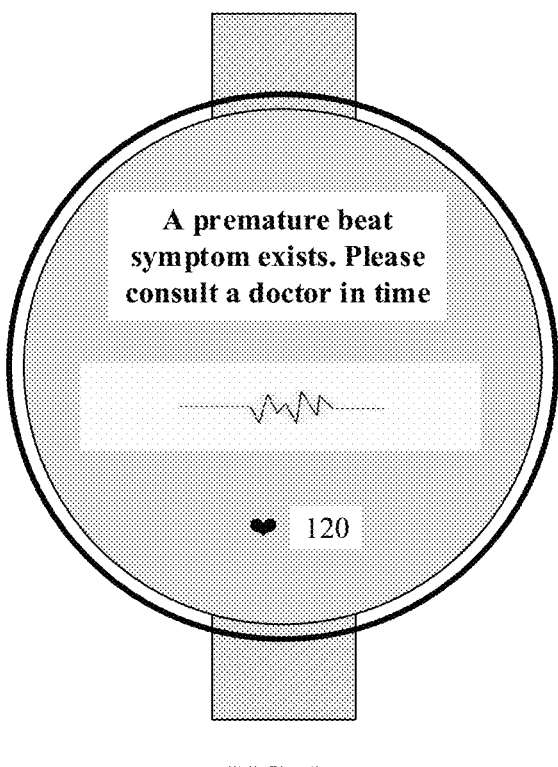
FIG. 5a is a schematic diagram of an interface of a watch according to an embodiment of this application.

If the premature beat load is greater than the premature atrial contraction threshold, a408 is performed, that is, the watch 100 reminds the user of a high risk of a premature beat (as shown in FIG. 5a). If the premature beat load is less than the premature atrial contraction threshold, a404 is performed.

a404: The watch 100 reminds the user to perform ECG measurement, and after the user provides an instruction of performing ECG measurement, the watch 100 performs ECG measurement and simultaneously performs PPG measurement. It can be understood that at the same time when the user is performing ECG measurement, a background of the watch 100 can simultaneously perform PPG measurement. It can be understood that, in some embodiments, ECG measurement may alternatively be automatically enabled without notifying the user after it is determined that a premature beat exists. Then, a405 is performed.

a405: The watch 100 determines a premature beat type based on an ECG waveform of ECG data, and marks a PPG waveform of continuously detected PPG data based on the premature beat type. In FIG. 3a and FIG. 3b, if a premature beat occurs during heart beating, the watch 100 generates corresponding abnormal ECG and PPG waveforms. If a P wave and a QRS complex appear in advance in the ECG waveform, the premature beat type is premature atrial contraction, and the watch 100 marks a distorted PPG unit wave generated in a corresponding time as a "premature atrial contraction" PPG unit wave. If a broad distorted R wave appears in the ECG waveform, the premature beat type is premature ventricular contraction, and the watch 100 marks a distorted PPG unit wave generated in a corresponding time as a "premature ventricular contraction" PPG unit wave. Then the watch 100 marks, based on shapes of the "premature atrial contraction" PPG unit wave and the "premature ventricular contraction" PPG unit wave, PPG waveforms of PPG data detected within a preset time. It can be understood that using an ECG to identify premature atrial contraction or premature ventricular contraction is merely an example, and an actually used algorithm is far more complex than that of the description, or a premature beat may even be marked by a doctor in a background to improve accuracy of premature beat diagnosis. For example, if it is detected, by using an ECG, that the premature beat type of the user is premature atrial contraction, waveform matching may be performed to search for a unit wave that is similar to or the same as the marked premature atrial contraction PPG unit wave and that is in a PPG waveform within 24 hours before and after the premature beat type is determined, and the found unit wave is marked as a "premature atrial contraction" unit wave. If it is detected, by using an ECG, that the premature beat type of the user is premature ventricular contraction, waveform matching may be performed to search for a unit wave that is similar to or the same as the marked premature ventricular contraction PPG unit wave and that is in a PPG waveform within 24 hours before and after the premature beat type is determined, and the found unit wave is marked as a "premature ventricular contraction" unit wave. It can be understood that the use of 24 hours is merely an example, and another value may be used, which is not limited herein. A time period for the marked PPG unit wave may be 24 hours before the premature beat type is detected, or may be 24 hours after the premature beat type is detected, or may be 24 hours before and after the premature beat type is detected, which is not limited herein.

If the watch 100 determines that the premature beat type is premature ventricular contraction, a406 is performed. If the watch 100 determines that the premature beat type is premature atrial contraction, a407 is performed.

a406: The watch 100 determines whether premature ventricular contraction load is greater than a premature ventricular contraction threshold. For example, the premature ventricular contraction load may be determined based on a percentage of a quantity of PPG unit waves marked as "premature ventricular contraction" in a PPG waveform represented by PPG data within a preset time in a total quantity of PPG unit waves. For example, within 24 hours, there are 100,000 PPG unit waves in a PPG waveform diagram, and 600 PPG unit waves marked as "premature ventricular contraction". In this case, the premature ventricular contraction load is 0.6%. It can be understood that 600 is merely an example, or another value may be used, which is not limited herein.

If it is determined that the premature ventricular contraction load is greater than the premature ventricular contraction threshold, a408 is performed, that is, the watch 100 reminds the user of a high risk of premature ventricular contraction. For a reminding manner, refer to the description of FIG. 5a. For example, when the watch 100 detects that the premature ventricular contraction load of the user is greater than the premature ventricular contraction threshold, an interface of the watch 100 displays reminder information such as "You have a symptom of premature ventricular contraction. Please seek medical attention in time". Otherwise, a401 is performed.

a407: The watch 100 determines whether premature atrial contraction load is greater than a premature atrial contraction threshold. For example, the premature atrial contraction load may be a percentage of a quantity of PPG unit waves marked as "premature atrial contraction" in a PPG waveform represented by PPG data within a preset time in a total quantity of PPG unit waves. For example, within 24 hours, there are 100,000 PPG unit waves in a PPG waveform diagram, and 12,000 PPG unit waves marked as "premature atrial contraction". In this case, the premature atrial contraction load is 12%. It should be noted that the values appearing in the examples above are merely examples, and other values may be used, which is not limited herein.

If it is determined that the premature atrial contraction load is greater than the premature atrial contraction threshold, a408 is performed, that is, the watch 100 reminds the user of a high risk of premature atrial contraction. For a reminding manner, refer to the description of FIG. 5a. For example, when the watch 100 detects that the premature atrial contraction load of the user is greater than the premature atrial contraction threshold, the interface of the watch 100 displays reminder information such as "You have a symptom of premature atrial contraction. Please seek medical attention in time". Otherwise, a401 is performed.

Figures 1, 4B:
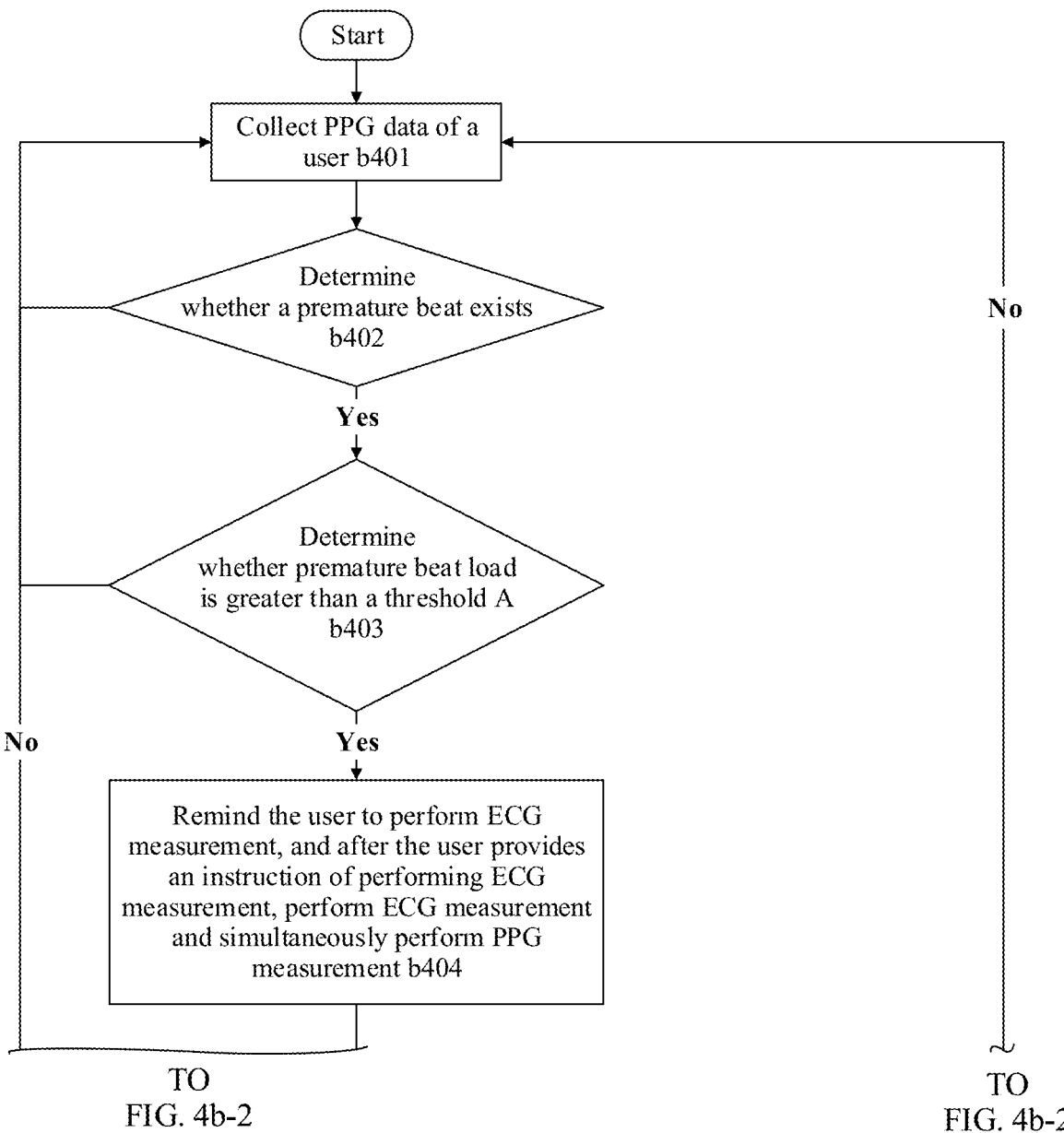
Figures 2, 4B:
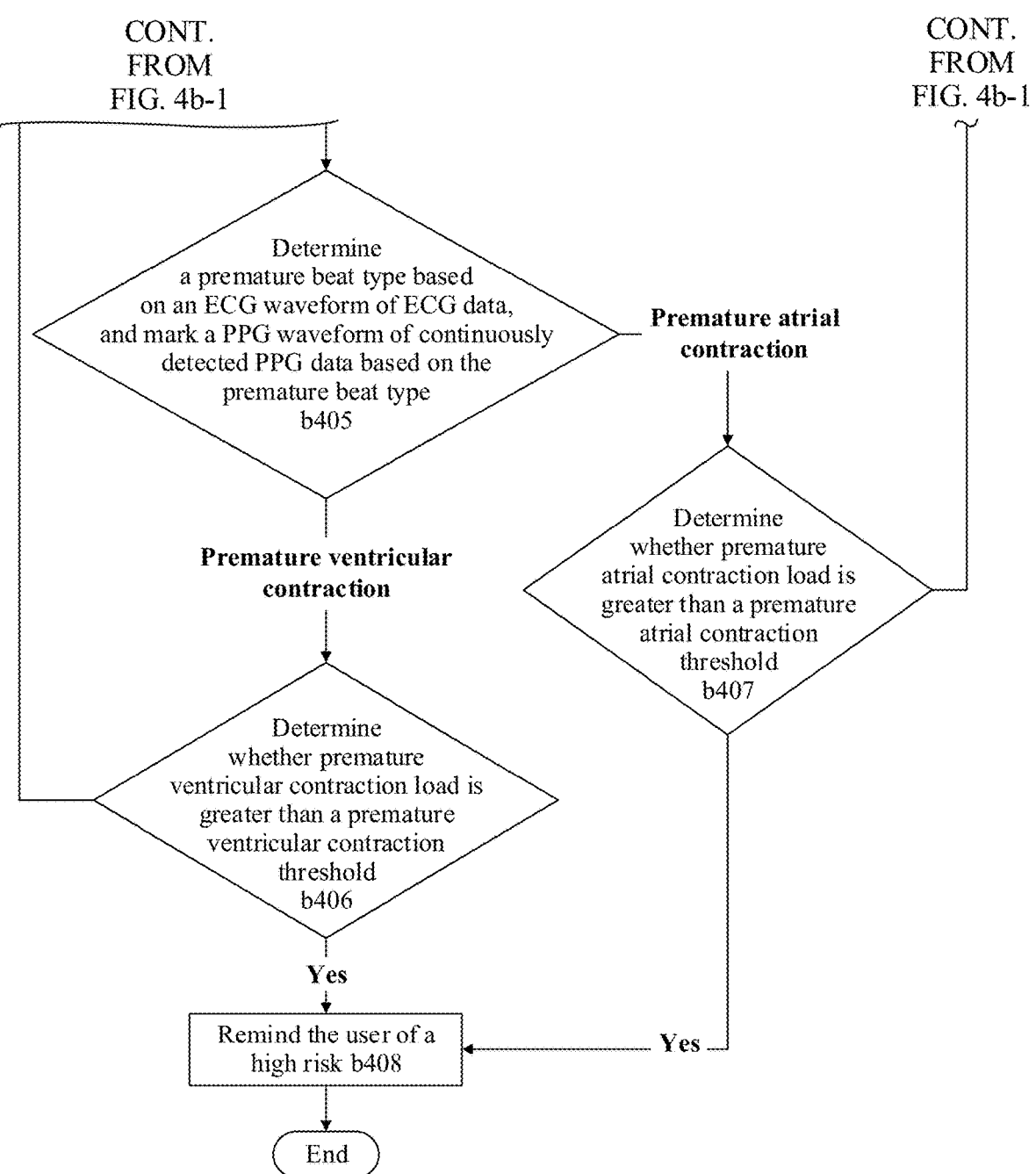

FIG. 4b-1 and FIG. 4b-2 are a flowchart of a premature beat detection method according to some other embodiments of this application. In the embodiment shown in FIG. 4b-1 and FIG. 4b-2, a relatively small threshold A is set first, and the threshold A is less than the premature ventricular contraction threshold (for example, 0.5%). When it is detected, in the PPG data, that the premature beat load is greater than the threshold A, it means that the user has a premature beat symptom, and the user may be reminded of a medium risk of a premature beat. Then the user is reminded to enable ECG detection or ECG detection is automatically performed. After that, the premature beat type is determined based on ECG detection data, and then the user is reminded of premature beat risks based on different types of premature beat thresholds, to avoid missing a premature ventricular contraction risk when the premature beat load is relatively low.

Specifically, as shown in FIG. 4b-1 and FIG. 4b-2, a procedure of the premature beat detection method includes the following steps.

b401: A watch 100 collects PPG data of a user.

b402: The watch 100 determines whether a premature beat exists (refer to the description of FIG. 4a-1 and FIG. 4a-2).

If a premature beat exists, b403 is performed, that is, the watch 100 determines whether premature beat load is greater than the threshold A, where the threshold A is less than or equal to a premature ventricular contraction threshold. For example, if the premature ventricular contraction threshold is 0.5%, the threshold A may be 0.3%. It should be noted that the values appearing in the examples above are merely examples, and other values may be used, which is not limited herein.

If the premature beat load is greater than the threshold A, b404 is performed, that is, the watch 100 may remind the user of a medium risk of a premature beat, and remind the user to perform ECG measurement. After the user provides an instruction of performing ECG measurement, the watch 100 performs ECG measurement and simultaneously performs PPG measurement. If the premature beat load is less than the threshold A, b401 is continuously performed.

b405: The watch 100 determines a premature beat type based on an ECG waveform of ECG data, and marks a PPG waveform of continuously detected PPG data based on the premature beat type (for a specific marking method, refer to related description of FIG. 4a-1 and FIG. 4a-2). If the watch 100 determines that the premature beat type is premature ventricular contraction, b406 is performed. If the watch 100 determines that the premature beat type is premature atrial contraction, b407 is performed.

b406: The watch 100 determines whether premature ventricular contraction load is greater than a premature ventricular contraction threshold (for a specific determining method, refer to the description of FIG. 4a-1 and FIG. 4a-2). If it is determined that the premature ventricular contraction load is greater than the premature ventricular contraction threshold, b408 is performed, that is, the watch 100 reminds the user of a high risk of premature ventricular contraction. Otherwise, b401 is continuously performed. A process of calculating the premature ventricular contraction load and a process of determining a premature ventricular contraction risk are the same as those in related description of FIG. 4a-1 and FIG. 4a-2. Details are not described herein again.

b407: The watch 100 determines whether premature atrial contraction load is greater than a premature atrial contraction threshold (refer to the description of FIG. 4a-1 and FIG. 4a-2). If it is determined that the premature atrial contraction load is greater than the premature atrial contraction threshold, b408 is performed, that is, the watch 100 reminds the user of a high risk of premature atrial contraction. Otherwise, b408 is continuously performed. A process of calculating the premature atrial contraction load and a process of determining a premature atrial contraction risk are the same as those in related description of FIG. 4a-1 and FIG. 4a-2. Details are not described herein again.

Figures 1, 4C:
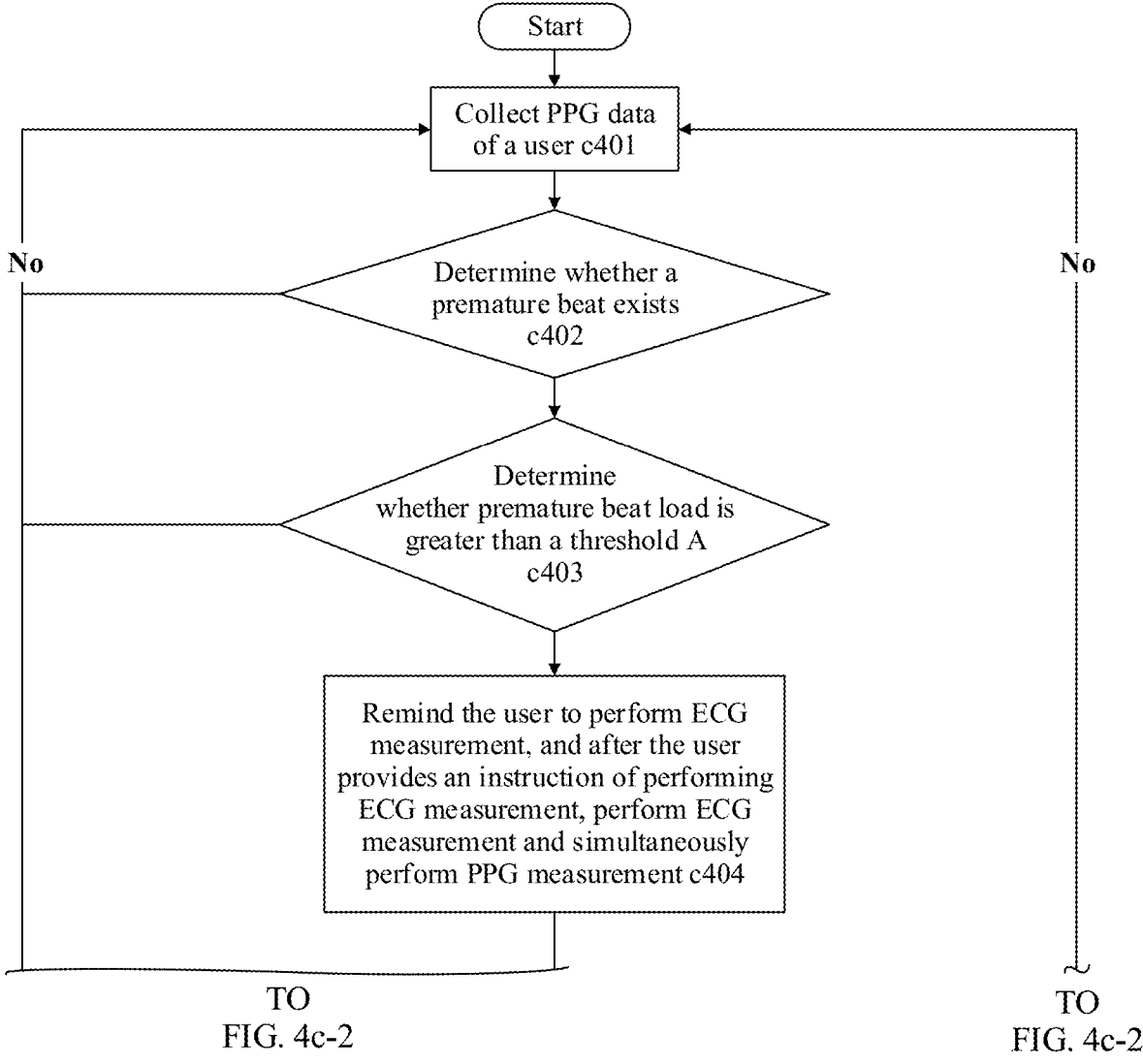
Figures 2, 4C:
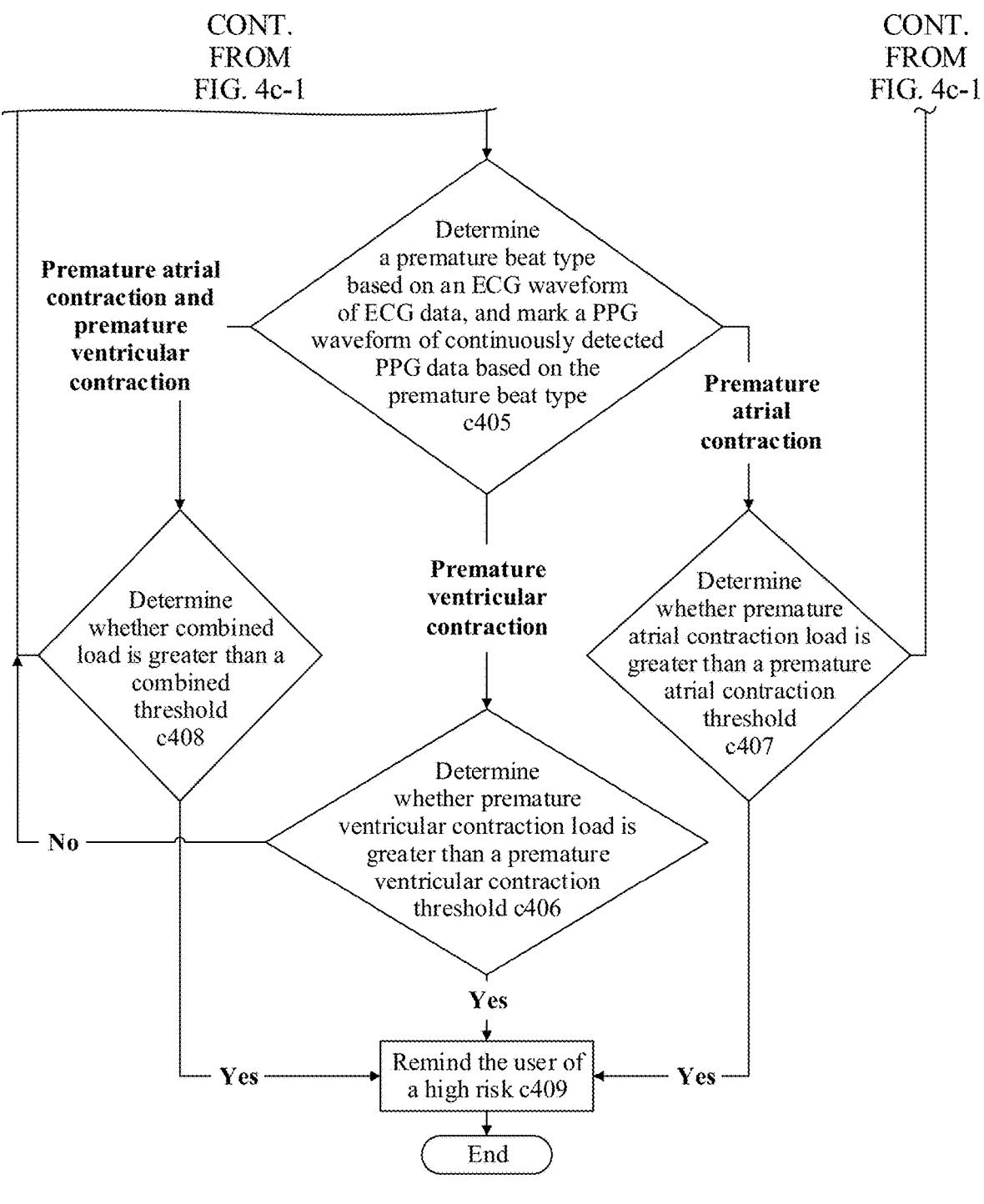

FIG. 4c-1 and FIG. 4c-2 are a flowchart of a premature beat detection method according to some embodiments of this application. In the embodiment shown in FIG. 4c-1 and FIG. 4c-2, a detection method is considered when a user has both two premature beat types: premature atrial contraction and premature ventricular contraction.

Specifically, as shown in FIG. 4c-1 and FIG. 4c-2, a procedure of the premature beat detection method includes the following steps.

c401: A watch 100 collects PPG data of the user.

c402: The watch 100 determines whether a premature beat exists. A determining process is the same as that in related description of FIG. 4a-1 and FIG. 4a-2. Details are not described herein again.

If a premature beat exists, c403 is performed, that is, the watch 100 determines whether premature beat load is greater than a threshold A. A determining process is the same as that in related description of FIG. 4b-1 and FIG. 4b-2. Details are not described herein again.

If the premature beat load is greater than the threshold A, c404 is performed, that is, the watch 100 may remind the user of a medium risk of a premature beat, and remind the user to perform ECG measurement. After the user provides an instruction of performing ECG measurement, the watch 100 performs ECG measurement and simultaneously performs PPG measurement.

If the premature beat load is less than the threshold A, c401 is continuously performed.

c405: The watch 100 determines a premature beat type based on an ECG waveform of ECG data, and marks a PPG waveform of continuously detected PPG data based on the premature beat type (for a specific marking method, refer to related description of FIG. 4a-1 and FIG. 4a-2).

If the watch 100 determines that the premature beat type is premature ventricular contraction, c406 is performed. If the watch 100 determines that the premature beat type is premature atrial contraction, c407 is performed. If it is determined that the premature beat type includes both premature atrial contraction and premature ventricular contraction, c408 is performed.

c406: The watch 100 determines whether premature ventricular contraction load is greater than a premature ventricular contraction threshold (refer to the description of FIG. 4a-1 and FIG. 4a-2).

If it is determined that the premature ventricular contraction load is greater than the premature ventricular contraction threshold, c409 is performed, that is, the user is reminded of a high risk of premature ventricular contraction. A process of calculating the premature ventricular contraction load and a process of determining a premature ventricular contraction risk are the same as those in related description of FIG. 4a-1 and FIG. 4a-2. Details are not described herein again. Otherwise, c401 is continuously performed.

c407: The watch 100 determines whether premature atrial contraction load is greater than a premature atrial contraction threshold (refer to the description of FIG. 4a-1 and FIG. 4a-2).

If the watch 100 determines that the premature atrial contraction load is greater than the premature atrial contraction threshold, c409 is performed, that is, the watch 100 reminds the user of a high risk of premature atrial contraction. Otherwise, c401 is continuously performed. A process of calculating the premature atrial contraction load and a process of determining a premature atrial contraction risk are the same as those in related description of FIG. 4a-1 and FIG. 4a-2. Details are not described herein again.

c408: The watch 100 determines whether combined load is greater than a combined threshold.

The combined threshold is a risk warning threshold when a patient has two symptoms: premature atrial contraction and premature ventricular contraction. Different impact of premature atrial contraction and premature ventricular contraction is comprehensively considered for the threshold, which is obtained under guidance of experts by using weighted construction of premature atrial contraction and premature ventricular contraction. It can be understood that the combined threshold may be a value between the premature ventricular contraction threshold and the premature atrial contraction threshold, or may be less than the premature ventricular contraction threshold or greater than the premature atrial contraction threshold, which is not limited herein. The descriptions below are merely examples. For a specific rule, refer to medical knowledge and advice of professional physicians when making the rule. For example, if the premature ventricular contraction threshold is 0.5% and the premature atrial contraction threshold is 10%, 20 pieces of premature atrial contraction load are equivalent to 1 piece of premature ventricular contraction load or 1 piece of premature atrial contraction load is equivalent to 0.05 pieces of premature ventricular contraction load. During calculation, the premature atrial contraction load may be converted into the premature ventricular contraction load, and the premature ventricular contraction threshold is used for determining. For example, within 24 hours, a heart beats 100,000 times, and there are 6000 "premature atrial contraction" unit waves and 400 "premature ventricular contraction" unit waves in a PPG waveform. In this case, 6000 "premature atrial contraction" unit waves are equivalent to 300 "premature ventricular contraction" unit waves, and the combined load is 700/100,000*100%=0.7%. The combined load is greater than the combined threshold (for example, 0.5%, this threshold is merely an example, and is not necessarily consistent with the premature ventricular contraction threshold), and the user needs to be reminded of a premature beat risk. It can be understood that, if the combined threshold is not considered, both premature atrial contraction and premature ventricular contraction of the patient are less than a corresponding premature atrial contraction threshold (for example, 10%) and a corresponding premature ventricular contraction threshold (for example, 0.5%). In this case, the patient is not reminded of a premature beat risk, and a potential risk may be ignored.

In addition, during calculation, alternatively, the premature ventricular contraction load may be converted into the premature atrial contraction load, and a combined threshold (for example, 10%, where 10% is merely an example, and may not necessarily be consistent with the separate premature ventricular contraction threshold) based on the premature atrial contraction threshold is used for determining. For example, if the premature ventricular contraction threshold is 0.5% and the premature atrial contraction threshold is 10%, 1 piece of premature ventricular contraction load is equivalent to 20 pieces of premature atrial contraction load. For example, within 24 hours, a heart beats 100,000 times, and there are 5000 "premature atrial contraction" unit waves and 300 "premature ventricular contraction" unit waves in a PPG waveform. In this case, 300 "premature ventricular contraction" unit waves are equivalent to 6000 "premature ventricular contraction" unit waves, and the combined load is 11,000/100,000=11%. The combined load is greater than the combined threshold 10%. It can be understood that, if the combined threshold is not considered, both premature atrial contraction and premature ventricular contraction of the patient are less than a corresponding premature atrial contraction threshold (for example, 10%) and a corresponding premature ventricular contraction threshold (for example, 0.5%). In this case, the patient is not reminded of a premature beat risk, and a potential risk may be ignored. It should be noted that the values appearing in the examples above are merely examples, and other values may be used, which is not limited herein.

If the combined load is greater than the combined threshold, c409 is performed, that is, the watch 100 reminds the user of a high risk of both premature atrial contraction and premature ventricular contraction. For a reminding manner, refer to the description of FIG. 5a. For example, an interface of the watch 100 displays reminder information such as "You have symptoms of both premature ventricular contraction and premature atrial contraction. Please seek medical attention immediately". Otherwise, c401 is performed.

Figure 4D:
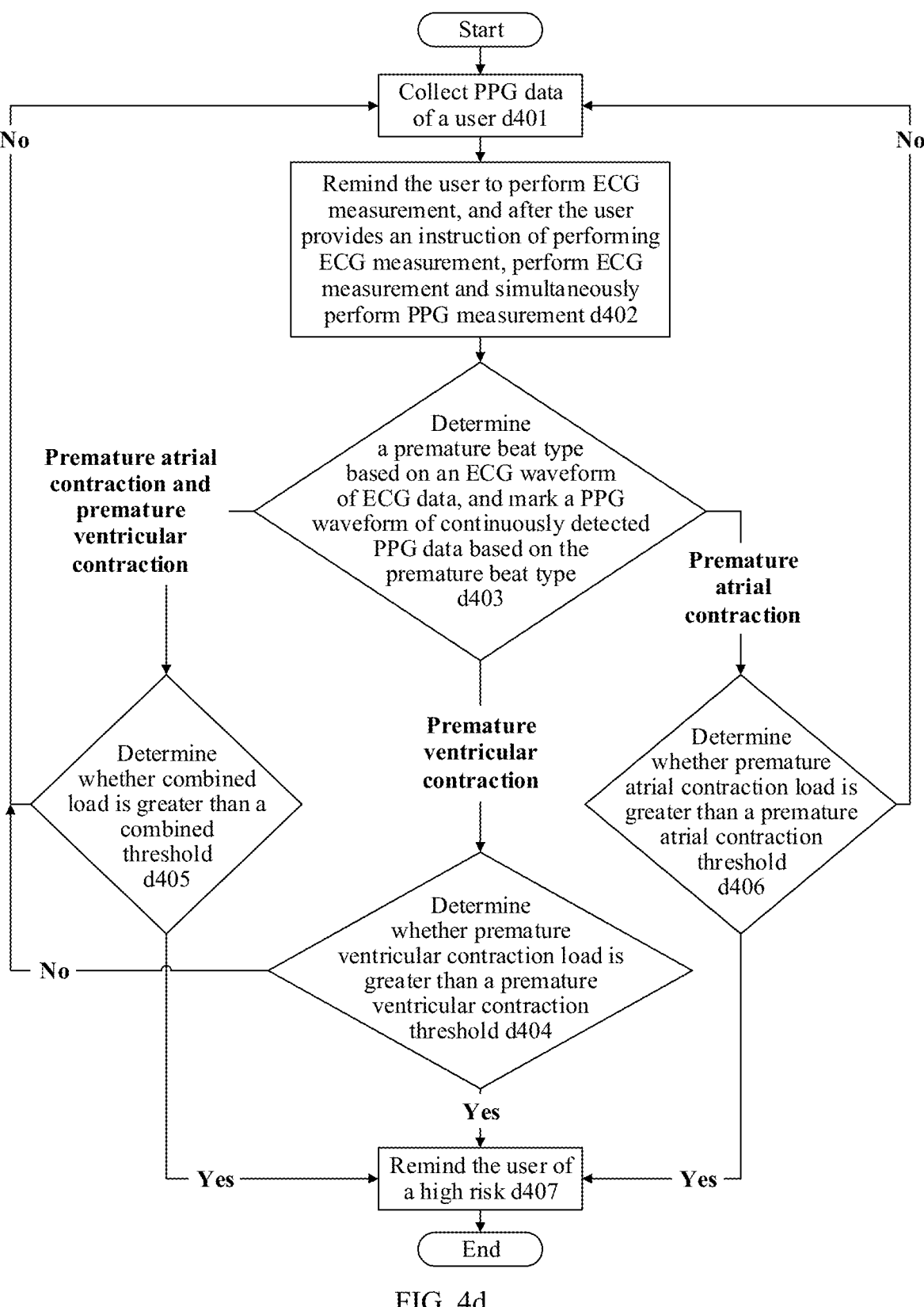
FIG. 4d is a schematic flowchart of a premature beat detection method according to an embodiment of this application.

FIG. 4d is a flowchart of a premature beat detection method according to some embodiments of this application.

In the embodiment shown in FIG. 4d, a user can directly perform ECG and PPG measurement without reminding the user by using a watch to perform ECG detection. Therefore, the user can determine, at any time, whether a high risk of a premature beat exists.

Specifically, as shown in FIG. 4d, a procedure of the premature beat detection method includes the following steps.

d401: A watch 100 collects PPG data of the user.

d402: The user performs ECG measurement, and after the user provides an instruction of performing ECG measurement, the watch 100 performs ECG measurement and simultaneously performs PPG measurement. In some embodiments, the watch automatically enables PPG measurement without notifying the user.

d403: The watch 100 determines a premature beat type based on an ECG waveform of ECG data, and marks a PPG waveform of continuously detected PPG data based on the premature beat type (for a specific marking method, refer to related description of FIG. 4a-1 and FIG. 4a-2).

If the watch 100 determines that the premature beat type is premature ventricular contraction, d404 is performed. If the watch 100 determines that the premature beat type is premature atrial contraction, d405 is performed. If it is determined that the premature beat type includes both premature atrial contraction and premature ventricular contraction, d406 is performed.

d404: The watch 100 determines whether premature ventricular contraction load is greater than a premature ventricular contraction threshold (for a specific determining method, refer to the description of FIG. 4a-1 and FIG. 4a-2).

If the watch 100 determines that the premature ventricular contraction load is greater than the premature ventricular contraction threshold, d407 is performed, that is, the watch 100 reminds the user of a high risk of premature ventricular contraction (refer to the description of FIG. 4a-1 and FIG. 4a-2). Otherwise, d401 is continuously performed.

d405: The watch 100 determines whether premature atrial contraction load is greater than a premature atrial contraction threshold (refer to the description of FIG. 4a-1 and FIG. 4a-2).

If the watch 100 determines that the premature atrial contraction load is greater than the premature atrial contraction threshold, d407 is performed, that is, the user is reminded of a high risk of premature atrial contraction. Otherwise, d401 is continuously performed. A process of calculating the premature atrial contraction load and a process of determining a premature atrial contraction risk are the same as those in related description of FIG. 4a-1 and FIG. 4a-2. Details are not described herein again.

d406: The watch 100 determines whether combined load is greater than a combined threshold (refer to the description of FIG. 4c-1 and FIG. 4c-2).

If the combined load is greater than the combined threshold, d407 is performed, that is, the user is reminded of a high risk of both premature atrial contraction and premature ventricular contraction (for details, refer to the description of FIG. 4c-1 and FIG. 4c-2). Otherwise, d401 is continuously performed. In the foregoing embodiments, the detection method when the user has a premature beat is described. However, in an actual case, the user sometimes has both atrial fibrillation and a premature beat. Atrial fibrillation means that a rate of atrial excitation reaches 300 to 600 beats per minute, and a ventricular rate is high (usually a heart rate is referred to as the ventricular rate), with an absolutely irregular rhythm, and sometimes reaches 100 to 160 beats per minute. A prevalence rate is closely related to diseases such as coronary heart diseases, hypertension, and heart failure. A patient with atrial fibrillation may be accompanied with premature beats, a common one of which is mainly premature ventricular contraction. A probability of atrial fibrillation accompanied with premature ventricular contraction accounts for about 90%.

Figure 6:
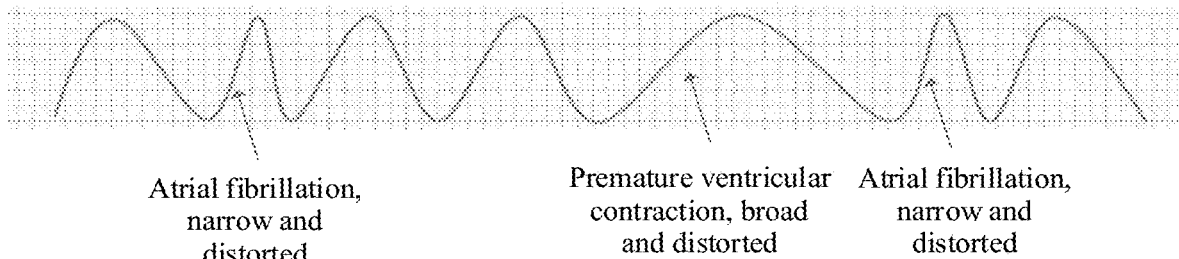
FIG. 6 is a schematic diagram of an atrial fibrillation waveform according to an embodiment of this application.

The following describes a detection method when a user has both atrial fibrillation and a premature beat. As shown in FIG. 6, when it is detected by using PPG that the user has atrial fibrillation, a PPG waveform shows a narrow and distorted waveform, which appears randomly, and a premature ventricular contraction PPG waveform is broad and distorted.

Figure 4E:
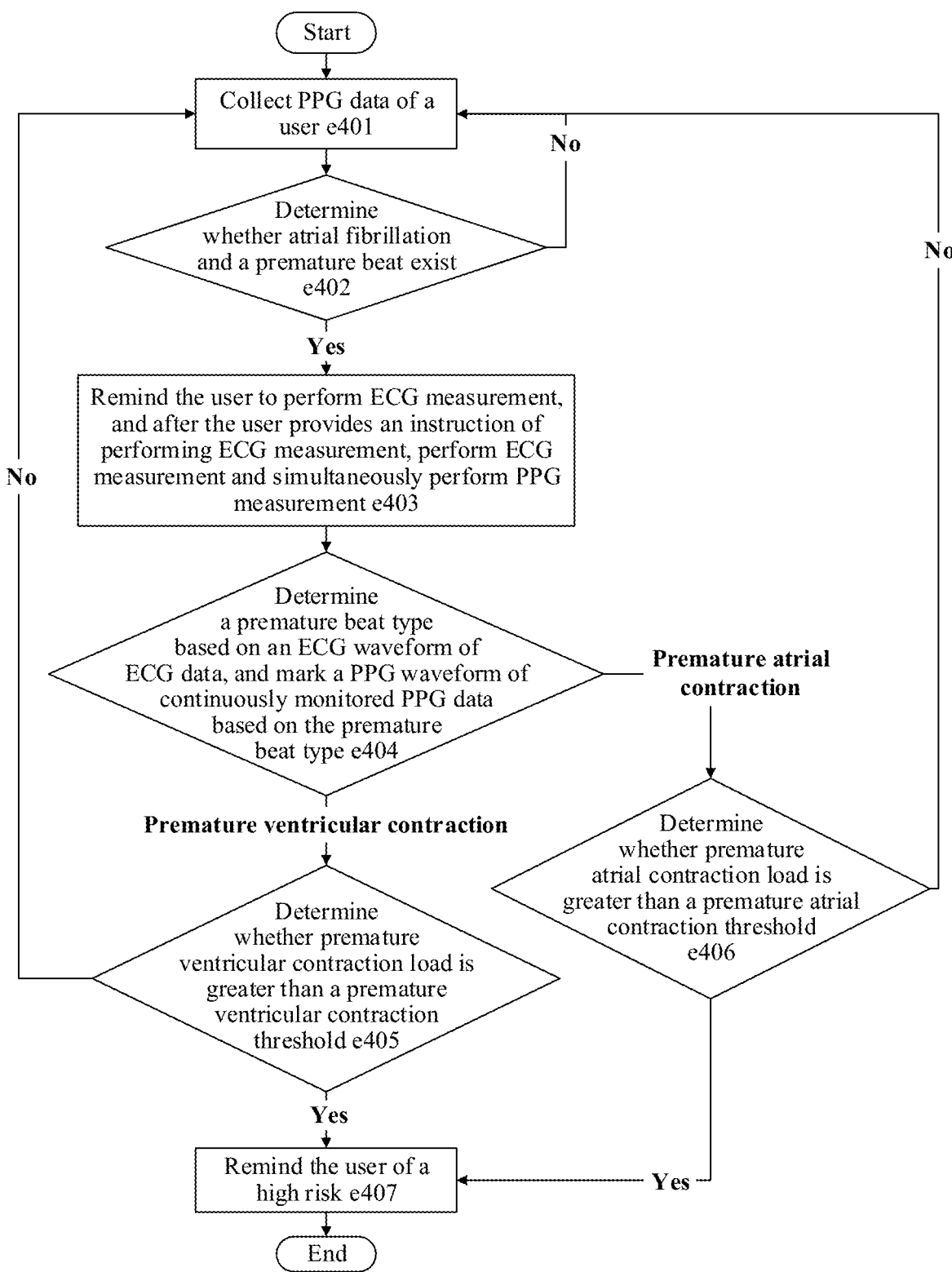
FIG. 4e is a schematic flowchart of a premature beat detection method according to an embodiment of this application.

Specifically, as shown in FIG. 4e, a detection procedure when both atrial fibrillation and a premature beat exist includes the following steps.

e401: A watch 100 collects PPG data of the user (refer to related description of FIG. 4a-1 and FIG. 4a-2).

e402: The watch 100 determines whether the user has atrial fibrillation and a premature beat (refer to related description of FIG. 4a-1 and FIG. 4a-2 and FIG. 6).

e403: If the user has atrial fibrillation and a premature beat, the watch 100 reminds the user to perform ECG measurement, and after the user provides an instruction (for example, the user taps a button on a display 102 of the watch 100, and in response to the tapping by the user, the watch 100 generates an enabling instruction) of performing ECG measurement, the watch 100 performs ECG measurement and simultaneously performs PPG measurement. Otherwise, e401 is continuously performed.

e404: The watch 100 determines a premature beat type based on an ECG waveform of ECG data, and marks a PPG waveform of continuously detected PPG data based on the premature beat type (refer to related description of FIG. 3a and FIG. 3b). If the watch 100 determines that the premature beat type is premature ventricular contraction, e405 is performed. If the watch 100 determines that the premature beat type is premature atrial contraction, e406 is performed.

e405: The watch 100 determines whether premature ventricular contraction load is greater than a premature ventricular contraction threshold (refer to related description of FIG. 4a-1 and FIG. 4a-2).

If the watch 100 determines that the premature ventricular contraction load is greater than the premature ventricular contraction threshold, e407 is performed, that is, the watch 100 reminds the user of a high risk of atrial fibrillation accompanied with premature ventricular contraction. For a reminding manner, refer to the description of FIG. 5a. For example, an interface of the watch 100 displays reminder information such as "You have a symptom of atrial fibrillation accompanied with premature ventricular contraction. Please seek medical attention immediately". Otherwise, e401 is performed.

e406: The watch 100 determines whether premature atrial contraction load is greater than a premature atrial contraction threshold (refer to related description of FIG. 4a-1 and FIG. 4a-2).

If the watch 100 determines that the premature atrial contraction load is greater than the premature atrial contraction threshold, e407 is performed, that is, the watch 100 reminds the user of a high risk of atrial fibrillation accompanied with premature atrial contraction. For a reminding manner, refer to the description of FIG. 5a. For example, the interface of the watch 100 displays reminder information such as "You have a symptom of atrial fibrillation accompanied with premature atrial contraction. Please seek medical attention immediately". Otherwise, e401 is performed.

Figure 5B:
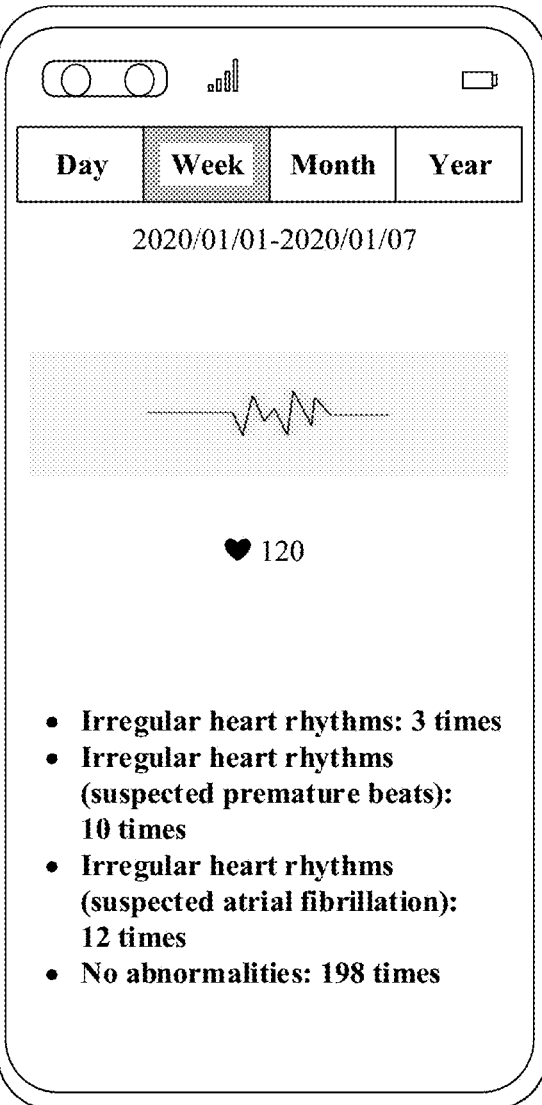
FIG. 5b is a schematic diagram of an interface of a mobile phone according to an embodiment of this application.

The foregoing embodiments describe solutions in which the watch 100 independently implements premature beat detection and user reminding. In another embodiment, alternatively, the watch 100 may be used for PPG detection and ECG detection, and another electronic device (such as a mobile phone 200 or a server 300) determines a premature beat type and calculates premature beat load (premature ventricular contraction load or premature atrial contraction load), and then returns a calculation result to the watch 100 to remind the user of a premature beat risk (refer to the description of FIG. 5a). Alternatively, the electronic device (such as the mobile phone 200) directly reminds the user of a premature beat risk. As shown in FIG. 5b, the mobile phone 200 may collect statistics on PPG data in a preset time, such as one day, one week, one month, or one year. For example, in one week, the following statistics are collected in total: there are 3 irregular heart rhythms, 10 irregular heart rhythms (suspected premature beats), 12 irregular heart rhythms (suspected atrial fibrillation), and 198 "no abnormalities". Based on the data, it can be obtained, through calculation, that a proportion of abnormal heart rhythms is 11%, which is greater than the premature atrial contraction threshold (10%). The mobile phone 200 reminds the user of a high risk of arrhythmia. For a reminding manner, refer to the premature beat risk reminding manner of the mobile phone in FIG. 5a. Details are not described herein again.

Figure 7:
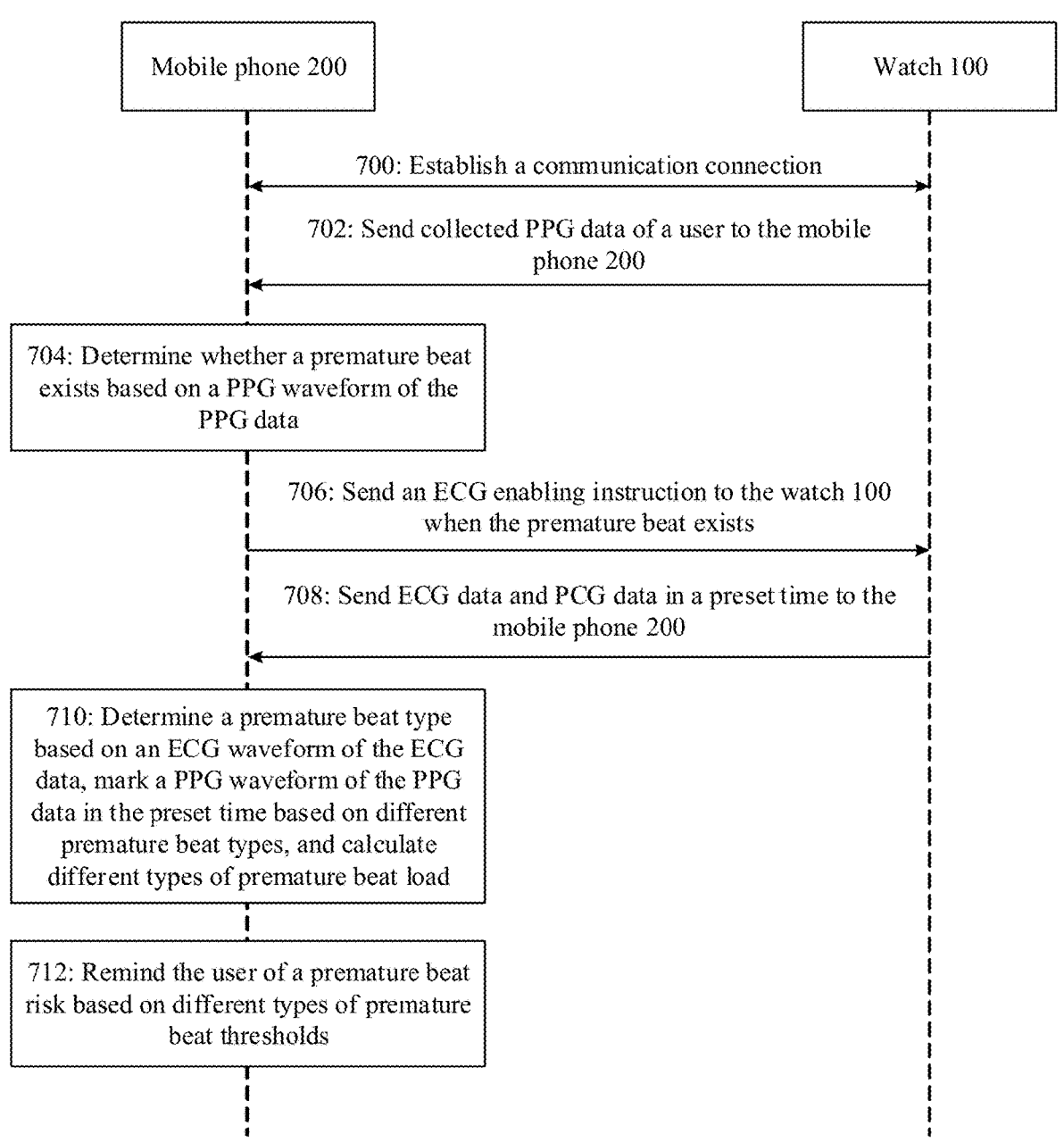
FIG. 7 is a schematic diagram of interaction between a mobile phone 200 and a watch 100 in a premature beat detection method according to some embodiments of this application.

Specifically, FIG. 7 is a schematic diagram of interaction between a mobile phone 200 and a watch 100. As shown in FIG. 7, the interaction includes the following steps.

700: The mobile phone 200 establishes a communication connection to the watch 100.

702: The watch 100 sends collected PPG data of a user to the mobile phone 200. It can be understood that the watch 100 may periodically send the collected PPG data to the mobile phone 200, or may send the collected PPG data in response to a request of the mobile phone 200, which is not limited herein.

704: The mobile phone 200 determines whether a premature beat exists based on a PPG waveform of the PPG data. A specific determining manner is the same as that on the watch 100 side. Details are not described herein again.

When a premature beat type determining result is that a premature beat exists, the mobile phone 200 sends an ECG enabling instruction to the watch 100. Otherwise, the mobile phone 200 skips sending a message to the watch 100.

706: When determining that the premature beat type determining result is that a premature beat exists, the mobile phone 200 sends an ECG enabling instruction to the watch 100. It can be understood that, in another embodiment, the mobile phone 200 may alternatively send the ECG enabling instruction to the user so that the user enables ECG detection by the watch 100.

708: The watch 100 sends ECG data and PPG data in a preset time to the mobile phone 200.

710: The mobile phone 200 determines the premature beat type based on an ECG waveform of the ECG data, marks a PPG waveform of the PPG data in the preset time based on different premature beat types, and then calculates different types of premature beat load. Specific determining and calculation manners are consistent with those on the watch 100 side. Details are not described herein again.

712: The mobile phone 200 reminds the user of a premature beat risk based on different types of premature beat thresholds, or the mobile phone 200 sends a calculation result to the watch 100 so that the watch 100 reminds the user of a premature beat risk, or the mobile phone 200 sends a calculation result to the watch 100 so that both the mobile phone 200 and the watch 100 remind the user of a premature beat risk. A manner in which the mobile phone 200 determines whether to remind the user of a premature beat risk is consistent with the determining manner on the watch 100 side. Details are not described herein again.

In the foregoing embodiments, the watch 100 performs premature beat detection by using ECG detection and PPG detection. It can be understood that in another embodiment, another electronic device may alternatively be used for premature beat detection.

For example, in some embodiments, an electronic mattress may be used for seismocardiogram (Seismocardiogram, SCG) detection, to determine whether a user has a premature beat, and then a watch 100 may be used for ECG detection, to determine a premature beat type and mark an SCG based on the premature beat type. Finally, the user is reminded of risks based on different types of premature beat thresholds. Details are as follows.

(1) The electronic mattress collects SCG data.

(2) The watch 100 performs ECG detection, and the electronic mattress synchronously performs SCG measurement.

(3) Determine a premature beat type based on an ECG waveform of the ECG data, and mark an SCG waveform of continuously detected SCG data based on the premature beat type. If the premature beat type is premature ventricular contraction, an SCG unit wave generated in a corresponding time can be marked as a "premature ventricular contraction" SCG unit wave. If the premature beat type is premature atrial contraction, an SCG unit wave generated in a corresponding time can be marked as a "premature atrial contraction" SCG unit wave.

(4) If it is determined that the premature beat type is premature ventricular contraction, determine whether premature ventricular contraction load is greater than a premature ventricular contraction threshold. The premature ventricular contraction load may be determined based on a percentage of a quantity of unit waves marked as "premature ventricular contraction" SCG unit waves in an SCG waveform within a preset time in a total quantity of SCG unit waves.

If the watch 100 determines that the premature beat type is premature atrial contraction, determine whether premature atrial contraction load is greater than a premature atrial contraction threshold. The premature atrial contraction load may be determined based on a percentage of a quantity of unit waves marked as "premature atrial contraction" SCG unit waves in an SCG waveform within a preset time in a total quantity of SCG unit waves.

(5) If the watch 100 determines that the premature ventricular contraction load is greater than the premature ventricular contraction threshold, remind the user of a high risk, or if the watch determines that the premature atrial contraction load is greater than the premature atrial contraction threshold, remind the user of a high risk.

In addition, in some embodiments, a body fat scale may also be used for ballistocardiogram (Ballistocardiogram, BCG) or impedance plethysmogram (Impedance plethysmogram, IPG) detection, to determine whether a user has a premature beat, and then a watch may be used for ECG detection, to determine a premature beat type and mark a BCG or an IPG based on the premature beat type. Finally, the user is reminded of risks based on different types of premature beat thresholds. The following is described by using an example in which the body fat scale performs BCG detection and the watch 100 performs ECG detection.

(1) The body fat scale collects BCG data.

(2) The watch 100 performs ECG detection, and the body fat scale synchronously performs BCG measurement.

(3) Determine a premature beat type based on an ECG waveform of ECG data, and mark a BCG waveform of continuously detected BCG data based on the premature beat type. If the premature beat type is premature ventricular contraction, a BCG unit wave generated in a corresponding time can be marked as a "premature ventricular contraction" BCG unit wave. If the premature beat type is premature atrial contraction, a corresponding BCG unit wave can be marked as a "premature atrial contraction" BCG unit wave.

(4) If the watch 100 determines that the premature beat type is premature ventricular contraction, determine whether premature ventricular contraction load is greater than a premature ventricular contraction threshold. The premature ventricular contraction load may be determined based on a percentage of a quantity of unit waves marked as "premature ventricular contraction" BCG unit waves in a BCG wave within a preset time in a total quantity of BCG unit waves in the BCG waveform.

If the watch 100 determines that the premature beat type is premature atrial contraction, determine whether premature atrial contraction load is greater than a premature atrial contraction threshold. The premature atrial contraction load may be determined based on a percentage of a quantity of unit waves marked as "premature atrial contraction" BCG unit waves in a BCG waveform within a preset time in a total quantity of BCG unit waves in the BCG waveform.

(5) If the watch 100 determines that the premature ventricular contraction load is greater than the premature ventricular contraction threshold, remind the user of a high risk, or if the watch determines that the premature atrial contraction load is greater than the premature atrial contraction threshold, remind the user of a high risk.

Figure 8:
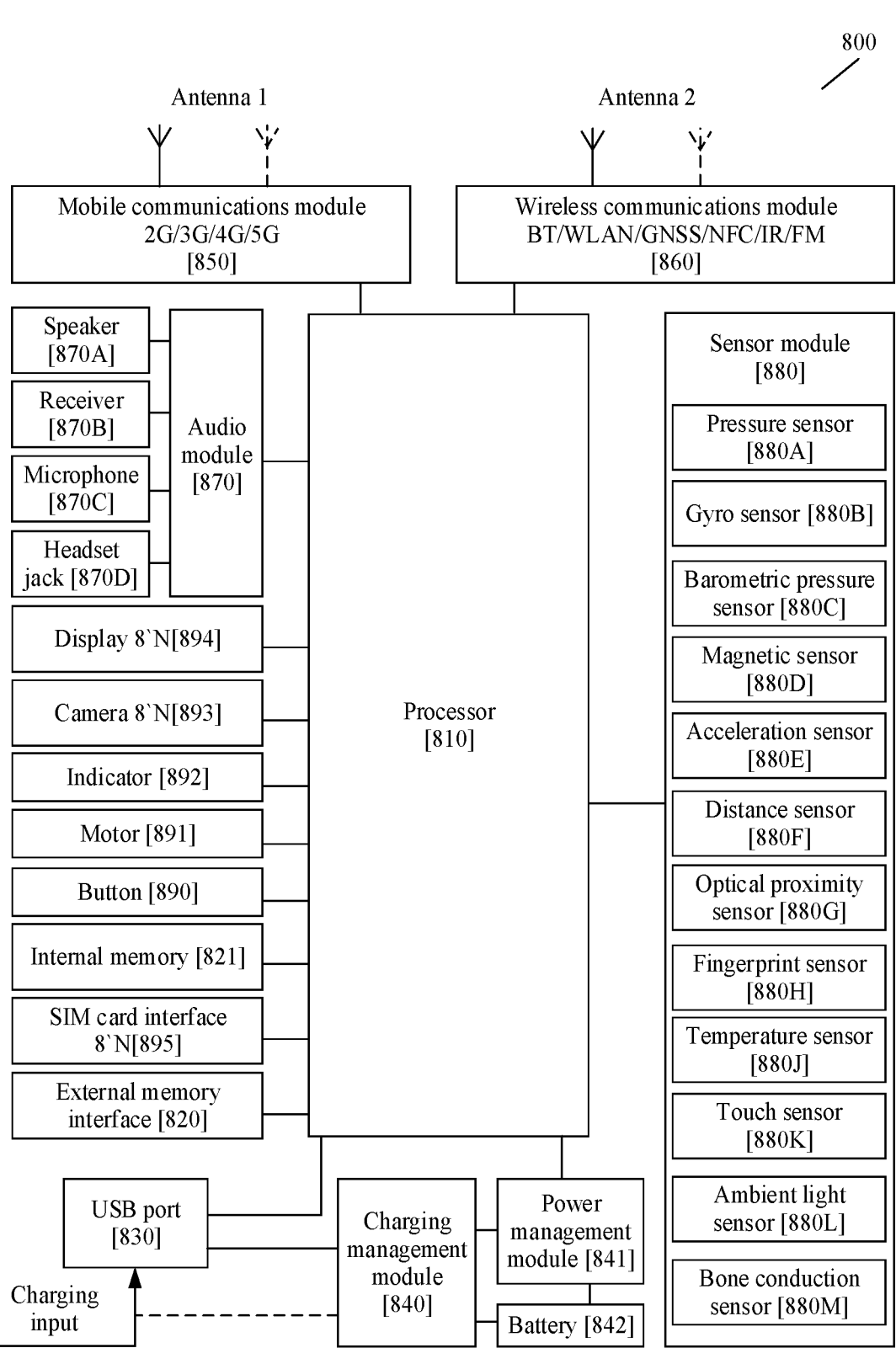
FIG. 8 is a schematic diagram of a structure of an electronic device 800 according to some embodiments of this application.

FIG. 8 is a block diagram of a structure of an electronic device 800 capable of implementing functions of the electronic device 200 shown in FIG. 1 according to an embodiment of this application. Specifically, as shown in FIG. 8, the electronic device 800 may include a processor 810, an external memory interface 820, an internal memory 821, a universal serial bus (universal serial bus, USB) port 830, a charging management module 840, a power management module 841, a battery 842, an antenna 1, an antenna 2, a mobile communications module 850, a wireless communications module 860, an audio module 870, a speaker 870A, a receiver 870B, a microphone 870C, a headset jack 870D, a sensor module 880, a button 890, a motor 898, an indicator 892, a camera 893, a display 894, a subscriber identification module (subscriber identification module, SIM) card interface 895, and the like. The sensor module 880 may include a pressure sensor 880A, a gyro sensor 880B, a barometric pressure sensor 880C, a magnetic sensor 880D, an acceleration sensor 880E, a distance sensor 880F, an optical proximity sensor 880G, a fingerprint sensor 880H, a temperature sensor 880J, a touch sensor 880K, an ambient light sensor 880L, a bone conduction sensor 880M, and the like.

It may be understood that a structure shown in this embodiment of this application does not constitute a specific limitation on the electronic device 800. In some other embodiments of this application, the electronic device 800 may include more or fewer components than those shown in the figure, combine some components, split some components, or have different component arrangements. The components shown in the figure may be implemented by using hardware, software, or a combination of software and hardware.

The processor 810 may include one or more processing units. For example, the processor 810 may include an application processor (AP), a modem processor, a graphics processing unit (GPU), an image signal processor (ISP), a controller, a video codec, a digital signal processor (DSP), a baseband processor, a neural-network processing unit (NPU), and/or the like. Different processing units may be independent devices, or may be integrated into one or more processors. The processor 810 may determine a premature beat type of a user based on received ECG data and calculate different types of premature beat load based on received PPG data.

The controller may generate an operation control signal based on an instruction operation code and a time sequence signal, to complete control of instruction fetching and instruction execution.

A memory may be disposed in the processor 810, and is configured to store an instruction and data. For example, the processor 810 may store PPG data and ECG data of a user that are sent by a watch 100. In some embodiments, the memory in the processor 810 is a cache. The memory may store an instruction or data that has been used or is cyclically used by the processor 810. If the processor 810 needs to use the instruction or the data again, the processor may directly invoke the instruction or the data from the memory. This avoids repeated access, reduces waiting time of the processor 810, and improves system efficiency.

In some embodiments, the processor 810 may include one or more interfaces. The interface may include an inter-integrated circuit (I2C) interface, an inter-integrated circuit sound (I2S) interface, a pulse code modulation (PCM) interface, a universal asynchronous receiver/transmitter (UART) interface, a mobile industry processor interface (MIPI), a general-purpose input/output (GPIO) interface, a subscriber identification module (SIM) interface, a universal serial bus (USB) port, and/or the like.

A micro USB port, a USB Type-C port, and the like may be included. The USB port 830 may be configured to connect to a charger to charge the electronic device 800, and may also be configured to transmit data between the electronic device 800 and a peripheral device, for example, transmit the PPG data and the ECG data of the user; or may be configured to connect to a headset, to play audio by using the headset. The port may be configured to connect to another electronic device such as an AR device.

It may be understood that an interface connection relationship between the modules that is shown in this embodiment of this application is merely an example for description, and does not constitute a limitation on a structure of the electronic device 800. In some other embodiments of this application, the electronic device 800 may alternatively use an interface connection manner different from that in the foregoing embodiment, or use a combination of a plurality of interface connection manners.

The charging management module 840 is configured to receive a charging input from the charger. The power management module 848 is configured to connect to the battery 842, the charging management module 840, and the processor 880. The power management module 848 receives an input from the battery 842 and/or the charging management module 840, and supplies power to the processor 880, the internal memory 821, the display 894, the camera 893, the wireless communications module 860, and the like. The power management module 848 may be configured to monitor parameters such as a battery capacity, a battery cycle count, and a battery state of health (electric leakage and impedance). In some other embodiments, the power management module 841 may alternatively be disposed in the processor 880. In some other embodiments, the power management module 841 and the charging management module 840 may also be provided in a same device.

A wireless communication function of the electronic device 800 may be implemented through the antenna 1, the antenna 2, the mobile communications module 850, the wireless communications module 860, the modem processor, the baseband processor, and the like.

The antenna 1 and the antenna 2 are configured to transmit and receive an electromagnetic wave signal. Each antenna in the electronic device 800 may be configured to cover one or more communication frequency bands. Different antennas may be multiplexed, to improve antenna utilization. For example, the antenna 1 may be multiplexed as a diversity antenna in a wireless local area network. In some other embodiments, an antenna may be used in combination with a tuning switch.

The mobile communications module 850 may provide a wireless communication solution that is applied to the electronic device 800 and that includes 2G, 3G, 4G, 5G, and the like. The wireless communications module 860 may provide a wireless communication solution that is applied to the electronic device 800 and that includes a wireless local area network (WLAN) (for example, a wireless fidelity (Wi-Fi) network), Bluetooth (BT), a global navigation satellite system (GNSS), frequency modulation (frequency modulation, FM), a near field communication (NFC) technology, an infrared (IR) technology, or the like. The wireless communications module 860 may be one or more components integrating at least one communications processor module. The wireless communications module 860 receives an electromagnetic wave through the antenna 2, performs frequency modulation and filtering processing on an electromagnetic wave signal, and sends a processed signal to the processor 810. The wireless communications module 860 may further receive a to-be-sent signal from the processor 810, perform frequency modulation and amplification on the signal, and convert the signal into an electromagnetic wave for radiation through the antenna 2.

In some embodiments, the electronic device 800 may communicate with the watch 100 by using the mobile communications module 850 or the wireless communications module 860. In some embodiments, the antenna 1 and the mobile communications module 850 in the electronic device 800 are coupled, and the antenna 2 and the wireless communications module 860 in the electronic device 800 are coupled, so that the electronic device 800 can communicate with a network and another device by using a wireless communications technology. The wireless communications technology may include a global system for mobile communications (GSM), a general packet radio service (GPRS), code division multiple access (CDMA), wideband code division multiple access (WCDMA), time-division code division multiple access (TD-SCDMA), long term evolution (LTE), BT, a GNSS, a WLAN, NFC, FM, an IR technology, and/or the like. The GNSS may include a global positioning system (GPS), a global navigation satellite system (GLONASS), a BeiDou navigation satellite system (BeiDou navigation satellite system, BDS), a quasi-zenith satellite system (QZSS), and/or satellite based augmentation systems (SBAS).

The electronic device 800 may implement a display function through the GPU, the display 894, the application processor, and the like. The GPU is a microprocessor for image processing, and is connected to the display 894 and the application processor. The GPU is configured to perform mathematical and geometric calculation, and render an image. The processor 810 may include one or more GPUs that execute program instructions to generate or change display information.

The electronic device 800 can implement a photographing function by using the ISP, the camera 893, the video codec, the GPU, the display 894, the application processor, and the like. In some embodiments of this application, the display 894 is configured to implement human-machine interaction with the user.

The external memory interface 820 may be used to connect to an external storage card, for example, a micro SD card, to extend a storage capability of the electronic device 800. The external storage card communicates with the processor 810 through the external memory interface 820, to implement a data storage function. For example, the ECG data and the PPG data of the user are stored into the external storage card.

The internal memory 821 may be configured to store computer-executable program code. The executable program code includes instructions. The internal memory 821 may include a program storage area and a data storage area. The program storage area may store an operating system, an application required by at least one function (for example, a sound playing function or an image playing function), and the like. The data storage area may store data (such as audio data and an address book) and the like that are created during use of the electronic device 800. In addition, the internal memory 821 may include a high-speed random access memory, and may further include a nonvolatile memory, for example, at least one magnetic disk storage device, a flash memory device, or a universal flash storage (universal flash storage, UFS). The processor 810 runs instructions stored in the internal memory 821 and/or instructions stored in the memory disposed in the processor, to perform various function applications and data processing of the electronic device 800.

The electronic device 800 may implement an audio function, for example, music playing and recording, through the audio module 870, the speaker 870A, the receiver 870B, the microphone 870C, the headset jack 870D, the application processor, and the like.

The button 890 includes a power button, a volume button, and the like. The button 890 may be a mechanical button, or may be a touch-sensitive button. The electronic device 800 may receive a button input, and generate a button signal input related to user settings and function control of the electronic device 800.

The motor 891 may generate a vibration prompt. The motor 891 may be configured to produce an incoming call vibration prompt and a touch vibration feedback. For example, touch operations performed on different applications (for example, photographing and audio playing) may correspond to different vibration feedback effects. For touch operations performed on different areas of the display 894, the motor 891 may also correspond to different vibration feedback effects. Different application scenarios (for example, time reminding, information receiving, an alarm clock, and a game) may also correspond to different vibration feedback effects. A touch vibration feedback effect may be customized.

The indicator 892 may be an indicator light, and may be configured to indicate a charging status and a power change, or may be configured to indicate a message, a missed call, a notification, and the like. The SIM card interface 895 is configured to connect to a SIM card.

Figure 9:
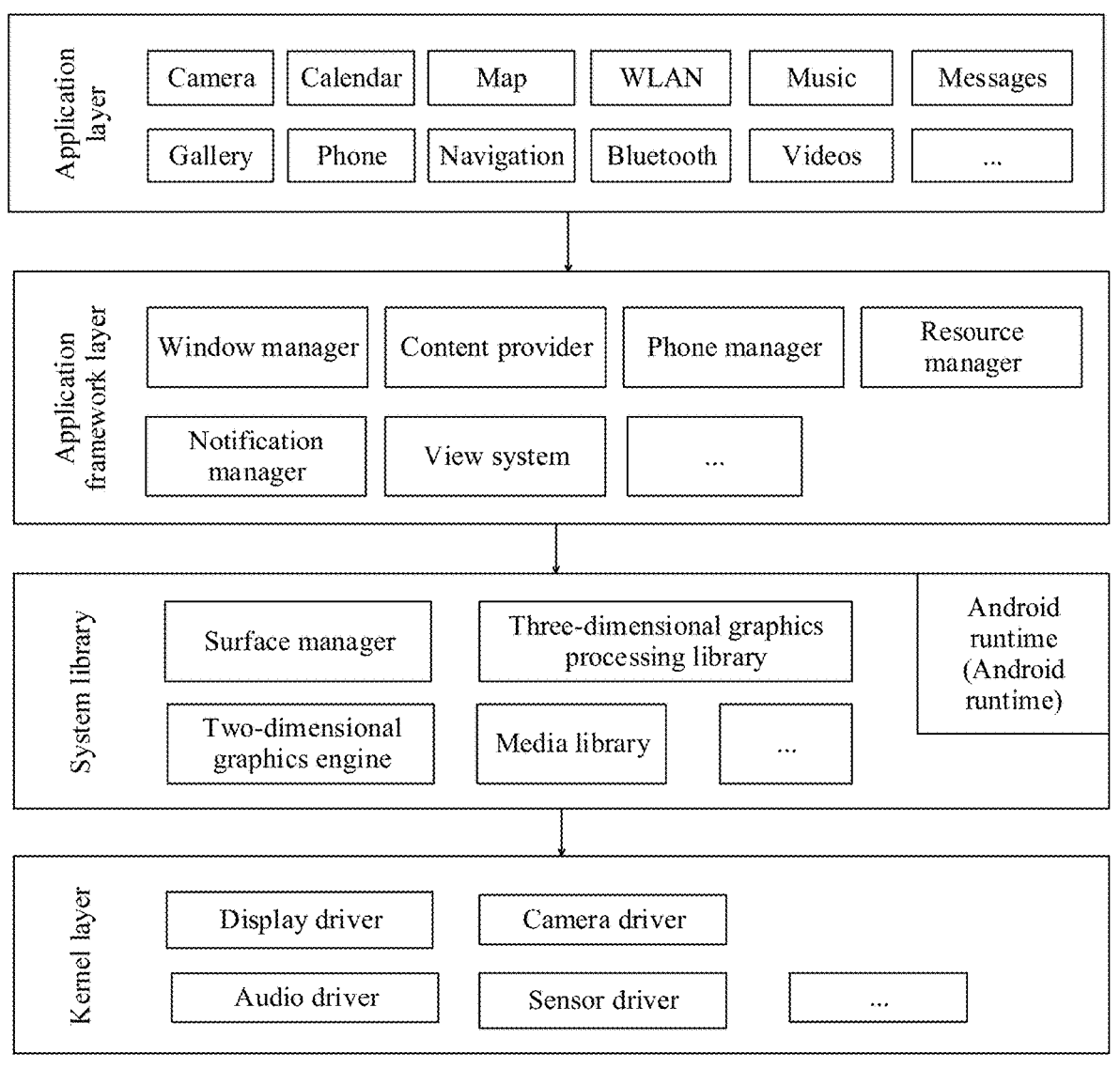
FIG. 9 shows a software system of an electronic device 800 according to some embodiments of this application.

Refer to FIG. 9. A software system of the electronic device 800 may use a layered architecture, an event-driven architecture, a microkernel architecture, a micro service architecture, or a cloud architecture. In this embodiment of this application, an Android system of a layered architecture is used as an example to describe a software structure of a terminal device. FIG. 9 is a block diagram of a software structure of a terminal device according to an embodiment of this application.

In a layered architecture, software is divided into several layers, and each layer has a clear role and task. The layers communicate with each other through a software interface. In some embodiments, the Android system is divided into four layers: an application layer, an application framework layer, an Android runtime (Android runtime) and system library, and a kernel layer from top to bottom.

The application layer may include a series of application packages. As shown in FIG. 9, the application packages may include applications such as Phone, Camera, Gallery, Calendar, Call, Map, Navigation, WLAN, Bluetooth, Music, Videos, and Messages.

The application framework layer provides an application programming interface (API) and a programming framework for an application at the application layer. The application framework layer includes some predefined functions. As shown in FIG. 9, the application framework layer may include a window manager, a content provider, a view system, a phone manager, a resource manager, a notification manager, and the like.

The window manager is configured to manage a window program. The window manager may obtain a size of a display, determine whether there is a status bar, perform screen locking, take a screenshot, and the like.

The content provider is configured to store and obtain data, and enable the data to be accessed by an application. The data may include a video, an image, audio, calls that are made and received, a browsing history and bookmarks, a phone book, and the like.

The view system includes visual controls, such as a control for displaying a text and a control for displaying an image. The view system may be configured to construct an application. A display interface may include one or more views. For example, a display interface including a notification icon of Messages may include a text display view and a picture display view.

The phone manager is configured to provide a communication function of the terminal device, for example, management of a call status (including answering, declining, or the like). The resource manager provides, for an application, various resources such as a localized character string, an icon, a picture, a layout file, and a video file.

The notification manager enables an application to display notification information in the status bar, and may be configured to transmit a notification-type message. The displayed information may automatically disappear after a short pause without user interaction. For example, the notification manager is configured to notify download completion, provide a message notification, and the like. The notification manager may alternatively be a notification that appears in a top status bar of the system in a form of a graph or a scroll bar text, for example, a notification of an application running on the background or a notification that appears on a screen in a form of a dialog window. For example, text information is displayed in the status bar, an announcement is given, the electronic device vibrates, or the indicator light blinks.

The Android runtime includes a kernel library and a virtual machine. The Android runtime is responsible for scheduling and management of the Android system.

The kernel library includes two parts: a function that needs to be called in Java language, and a kernel library of Android.

The application layer and the application framework layer run on the virtual machine. The virtual machine executes Java files at the application layer and the application framework layer as binary files. The virtual machine is configured to perform functions such as object lifecycle management, stack management, thread management, security and exception management, and garbage collection.

The system library may include a plurality of function modules, such as a surface manager, a media library, a three-dimensional graphics processing library (for example, OpenGL ES), and a 2D graphics engine (for example, SGL).

The surface manager is configured to manage a display subsystem and provide fusion of 2D and 3D layers for a plurality of applications.

The media library supports playback and recording of a plurality of commonly used audio and video formats, static image files, and the like. The media library may support a plurality of audio and video encoding formats, such as MPEG-4, H.264, MP3, AAC, AMR, JPG, PNG, and the like.

The three-dimensional graphics processing library is configured to implement three-dimensional graphics drawing, image rendering, composition, layer processing, and the like.

The 2D graphics engine is a drawing engine for 2D drawing.

The kernel layer is a layer between hardware and software. The kernel layer includes at least a display driver, a camera driver, an audio driver, and a sensor driver.

The use of "one embodiment" or "an embodiment" in the specification means that particular features, structures, or characteristics described with reference to the embodiment are included in at least one example implementation solution or technology in accordance with the present disclosure. The phrase "in one embodiment" appearing in various places in the specification does not necessarily all mean a same embodiment.

The present disclosure further relates to an operating apparatus configured to implement processes in the specification. The apparatus may be constructed dedicatedly for required purposes, or may include a general-purpose computer selectively activated or reconfigured by a computer program stored in a computer. Such a computer program may be stored on a computer-readable medium, such as but not limited to, any type of disk, including a floppy disk, an optical disc, a CD-ROM, a magneto-optical disk, a read only memory (ROM), a random access memory (RAM), an EPROM, an EEPROM, a magnetic or optical card, an application-specific integrated circuit (ASIC), and any type of medium suitable for storing electronic instructions. In addition, each of them may be coupled to a computer system bus. Moreover, the computer mentioned in the specification may include a single processor or may be an architecture using a plurality of processors for increased computing capabilities.

Processes and displays presented in the specification do not inherently relate to any specific computer or another apparatus. Various general-purpose systems may also be used together with programs of the teachings of the specification, or constructing more dedicated apparatuses to perform one or more method steps can be proved to be convenient. Structures used for various such systems are discussed in the following description. In addition, any specific programming language capable of implementing the technologies and implementation solutions of the present disclosure may be used. Various programming languages may be used to implement the present disclosure, as discussed in the specification.

In addition, the language used in the specification is already mainly selected for readability and instructional purposes and may not be selected to depict or limit the disclosed topics. Therefore, the present disclosure is intended to describe but not to limit the scope of the concepts discussed in the specification.

What is claimed is:

1. A premature beat detection method, comprising:
obtaining, by a first electronic device, photoplethysmography (PPG) detection data comprising a plurality of repeated normal first waves and at least one distorted first wave;
determining, based on the PPG detection data comprising the at least one distorted first wave, that a user has a premature beat;
obtaining, by the first electronic device, electrocardiograph (ECG) detection data comprising a plurality of repeated normal second waves and at least one distorted second wave;
determining, by the first electronic device, based on the PPG detection data comprising the at least one distorted first wave and the ECG detection data comprising the at least one distorted second wave, a premature beat type of the user;
calculating a premature beat load of the user based on the PPG detection data; and
reminding, by the first electronic device, the user of a premature beat risk when the calculated premature beat load is greater than a premature beat load threshold corresponding to the premature beat type.

2. The method according to claim 1, wherein the calculating the premature beat load of the user based on the ECG detection data and the PPG detection data comprises:
determining, by the first electronic device, based on the premature beat type, a shape of a unit wave that corresponds to the determined premature beat type and that is in a waveform of the PPG detection data;
matching, by the first electronic device based on the determined shape of the unit wave, a unit wave that corresponds to the determined premature beat type and that is in a waveform corresponding to the PPG detection data; and
calculating, by the first electronic device, the premature beat load of the user based on the matched unit wave corresponding to the determined premature beat type.

3. The method according to claim 2, wherein the premature beat load is a percentage of a quantity of matched unit waves corresponding to the determined premature beat type in a total quantity of unit waves in the waveform of the PPG detection data.

4. The method according to claim 1, wherein the determining, by the first electronic device, the premature beat type of the user comprises:
when it is determined, based on the first-PPG detection data, that the user has a premature beat, determining, by the first electronic device, whether the premature beat load is less than a premature atrial contraction threshold; and when the premature beat load is less than the premature atrial contraction threshold, determining, by the first electronic device, determine the premature beat type of the user, wherein
the premature beat type comprises premature atrial contraction and premature ventricular contraction, and the premature atrial contraction threshold is greater than a premature ventricular contraction threshold.

5. The method according to claim 4, further comprising:
when the premature beat load is greater than the premature atrial contraction threshold, reminding, by the first electronic device, the user of the premature beat risk.

6. The method according to claim 1, wherein the determining, by the first electronic device the premature beat type of the user comprises:
when it is determined, based on the PPG detection data, that the user has a premature beat, calculating, by the first electronic device, whether the premature beat load is greater than an enabling threshold; and
when the premature beat load is greater than the enabling threshold, determining the premature beat type of the user, wherein
the premature beat type comprises premature atrial contraction and premature ventricular contraction, a premature atrial contraction threshold is greater than a premature ventricular contraction threshold, and the premature ventricular contraction threshold is greater than the enabling threshold.

7. The method according to claim 1, further comprising:
when the first electronic device determines to remind the user of the premature beat risk, displaying, by the first electronic device, premature beat risk reminder information.

8. The method according to claim 1, wherein the obtaining, by the first electronic device, the first detection data further comprising:
obtaining, by the first electronic device, the PPG detection data by a PPG sensor, wherein the first electronic device comprises the PPG sensor;
wherein the obtaining, by the first electronic device, the ECG detection data further comprising:
obtaining, by the first electronic device, the ECG detection data by the PPG sensor and an ECG sensor, wherein the first device further comprises the ECG sensor.

9. The method according to claim 1, wherein the obtaining, by the first electronic device, the PPG detection data further comprising:
obtaining, by the first electronic device, the PPG detection data from a second electronic device;
the obtaining, by the first electronic device, the ECG detection data further comprising:
obtaining, by the first electronic device, the ECG detection data from the second electronic device.

10. An electronic device, comprising:
a non-transitory memory, configured to store instructions for execution by one or more processors of a system, and
a processor, being at least one of the processors of the electronic device, and configured to perform:
obtaining photoplethysmography (PPG) detection data comprising a plurality of repeated normal first waves and at least one distorted first wave;
determining, based on the PPG detection data comprising the at least one distorted first wave, that a user has a premature beat;

obtaining electrocardiograph (ECG) detection data comprising a plurality of repeated normal second waves and at least one distorted second wave;

determining based on the PPG detection data comprising the at least one distorted first wave and the ECG detection data comprising the at least one distorted second wave, a premature beat type of the user;

calculating premature beat load of the user based on the PPG detection data; and reminding the user of a premature beat risk when the calculated premature beat load is greater than a premature beat load threshold corresponding to the premature beat type.

11. The electronic device according to claim 10, wherein the processor is configured to perform:

obtaining the PPG detection data from a second electronic device; and obtaining the ECG detection data from the second electronic device.

12. The electronic device according to claim 10, wherein the processor is configured to perform:

determining based on the determined premature beat type, a shape of a unit wave that corresponds to the determined premature beat type and that is in a waveform of the PPG detection data;

matching based on the determined shape of the unit wave, a unit wave that corresponds to the determined premature beat type and that is in a waveform corresponding to the PPG detection data; and calculating the premature beat load of the user based on the matched unit wave corresponding to the determined premature beat type, wherein the premature beat load is a percentage of a quantity of matched unit waves corresponding to the determined premature beat type in a total quantity of unit waves in the waveform of the PPG detection data.

13. The electronic device according to claim 10, wherein the processor is configured to perform:

when it is determined, based on the PPG detection data, that the user has a premature beat, determining whether the premature beat load is less than a premature atrial contraction threshold; and when the premature beat load is less than the premature atrial contraction threshold, sending, the enabling instruction, wherein the premature beat type comprises premature atrial contraction and premature ventricular contraction, and the premature atrial contraction threshold is greater than a premature ventricular contraction threshold.

14. The electronic device according to claim 10, wherein the processor is configured to perform:

when it is determined, based on the PPG detection data, that the user has a premature beat, calculating whether the premature beat load is greater than an enabling threshold; and when the premature beat load is greater than the enabling threshold, sending the enabling instruction, wherein the premature beat type comprises premature atrial contraction and premature ventricular contraction, a premature atrial contraction threshold is greater than a premature ventricular contraction threshold, and the premature ventricular contraction threshold is greater than the enabling threshold.

15. The electronic device according to claim 10, wherein the processor is configured to perform:

displaying premature beat risk reminder information.

16. The electronic device according to claim 10, wherein the processor is configured to perform:

obtaining the PPG detection data by a PPG sensor, wherein the first electronic device comprises the PPG sensor; and obtaining the ECG detection data by ECG sensor, wherein the first device comprises the ECG sensor.

17. The electronic device according to claim 10, wherein the processor is configured to perform:

obtaining the PPG detection data from a second electronic device; and obtaining the ECG detection data from the second electronic device.

18. An electronic device, comprising:

a non-transitory memory, configured to store instructions for execution by one or more processors of a system, and a processor, being at least one of the processors of the electronic device, and configured to perform:

performing premature beat detection on a user by using a premature beat detection function, wherein the premature beat detection function causes detecting photoplethysmography (PPG) detection data comprising a plurality of repeated normal first waves and at least one distorted first wave;

sending the PPG detection data obtained by using the premature beat detection function to a second electronic device;

receiving an enabling instruction from the second electronic device;

enabling a premature beat type determining function in response to the enabling instruction, wherein the premature beat type determining function causes detecting electrocardiograph (ECG) detection data comprising a plurality of repeated normal second waves and at least one distorted second wave; and sending to the second electronic device, the ECG detection data obtained by using the premature beat detection function, and determining, based on the PPG detection data comprising the at least one distorted first wave and the ECG detection data comprising the at least one distorted second wave, a premature beat type of a user.

19. The electronic device according to claim 18, wherein the electronic device comprising a PPG sensor and an ECG sensor, the processor is configured to perform:

obtaining the PPG detection data by the PPG sensor; and obtaining the ECG detection data by the PPG sensor and the ECG sensor.

20. The electronic device according to claim 18, wherein the processor is configured to perform:

receiving premature beat risk reminder information from the second electronic device; and displaying the risk reminder information.

\* \* \* \* \*